United States Patent [19]

Umezawa et al.

[11] Patent Number: 4,529,549

[45] Date of Patent: Jul. 16, 1985

[54] SPERGUALIN-RELATED COMPOUNDS AND PROCESS FOR THE PREPARATION THEREOF

[75] Inventors: Hamao Umezawa; Tomio Takeuchi; Rinzo Nishizawa; Katsutoshi Takahashi, all of Tokyo; Teruya Nakamura, Kusatsu; Yoshihisa Umeda, Otsu, all of Japan

[73] Assignee: Zaidan Hojin Biseibutsu Kagaku Kenkyu Kai, Tokyo, Japan

[21] Appl. No.: 524,354

[22] Filed: Aug. 18, 1983

[30] Foreign Application Priority Data

Sep. 2, 1982 [JP] Japan ................... 57-151698

[51] Int. Cl.³ ............................ C07F 5/00; C07F 7/00
[52] U.S. Cl. .................. 260/404.5; 548/342; 548/504; 548/538
[58] Field of Search ............... 260/404.5 G; 548/342, 548/504, 538

[56] References Cited

U.S. PATENT DOCUMENTS

| | | | |
|---|---|---|---|
| 3,737,443 | 6/1973 | Hashimoto et al. | 260/404.5 G X |
| 3,935,266 | 1/1976 | Hashimoto et al. | 260/404.5 G X |
| 3,937,805 | 2/1976 | Harrison | 260/404.5 G |
| 4,416,899 | 11/1983 | Umezawa et al. | 424/320 |

FOREIGN PATENT DOCUMENTS 3217693 12/1982 Fed. Rep. of Germany .

OTHER PUBLICATIONS

Takeuchi et al., J. Antibiotics 34(12), 1619-1621, (1981).
Umezawa et al., J. Antibiotics 34(12), 1622-1623, (1981).
Kondo et al., J. Antibiotics 34(12), 1625-1627, (1981).

Primary Examiner—Helen M. S. Sneed
Attorney, Agent, or Firm—Henry C. Nields

[57] ABSTRACT

This invention relates to a novel spergualin-related compound and a process for the production thereof. The novel compound, which has a high antitumor activity, is represented by the general formula

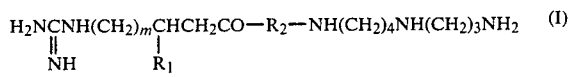

wherein $R_1$ represents a hydrogen atom, hydroxyl group, or an aliphatic acyloxy group having 1 to 10 carbon atoms, $R_2$ represents an amino acid residue (except for the residue of α-hydroxyglycine) formed by removing one hydrogen atom and hydroxyl group from respectively the α- or ω-amino group and the α-carboxyl group of an α- or ω-amino acid, said amino acid residue forming acid amide linkages with the adjacent carbonyl group and amino group, and m is an integer of 4 to 6.

6 Claims, No Drawings

SPERGUALIN-RELATED COMPOUNDS AND PROCESS FOR THE PREPARATION THEREOF

BACKGROUND OF THE INVENTION

Spergualin is a compound isolated from the culture filtrate of a spergualin-producing strain of the genus Bacillus by Umezawa et al., who are also the inventors of this invention. It has the following structure:

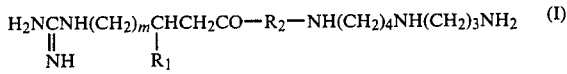

Spergualin exhibits a growth inhibitory activity against Gram-positive and -negative bacteria. In therapeutic experiments, it exhibits also a distinctive curing effect and life extension effect on mouse leukemia L-1210 and FL-4, Ehrlich carcinoma, and sarcoma 180 (S-180). So, it is a compound expected to be an antitumor agent (B.P. Publication No. 2,084,999A). It is known that spergualin can be obtained by chemical synthesis {J. Antibiotics, vol. 34, 1625 (1981)}.

It is also known that 15-deoxyspergualin, a deoxy derivative at position 15 of spergualin, has similar effects to those of spergualin. Further, Umezawa et al. conducted a research on 15-O-acylspergualin, which is an acyl derivative of the hydroxyl group at the position 15 of spergualin, and, as a result, found that this compound has also similar biological activities. Although these compounds have a distinguished carcinostatic activity, their insufficient stability in aqueous solution has hindered them from clinical application.

The present inventors further conducted an extensive study to find a spergualin-related compound which is stable in aqueous solution, yet retaining the antibiotic activity. As a result, this invention has been accomplished based on the finding that the above object can be achieved by converting the group

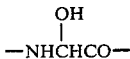

at positions 10 to 12 into various amino acid residues.

DETAILED DESCRIPTION OF THE INVENTION

This invention relates to a novel compound represented by the following general formula (I) or a salt thereof:

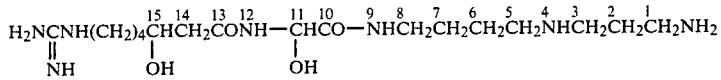

wherein $R_1$ represents a hydrogen atom, hydroxyl group, or an aliphatic acyloxy group having 1 to 10 carbon atoms, $R_2$ represents an amino acid residue (except for the residue of α-hydroxyglycine) formed by the removal of one hydrogen atom and hydroxyl group from respectively the α- or ω-amino group and the α-carboxyl group of an α- or ω-amino acid, said amino acid residue forming acid amide linkages with the adjacent carbonyl group and amino group, and m is an integer of 4 to 6. The invention also relates to a method for producing a spergualin-related compound represented by the general formula (I) or a salt thereof, which comprises removing the protecting groups in a known manner from a protected spergualin-related compound represented by the general formula

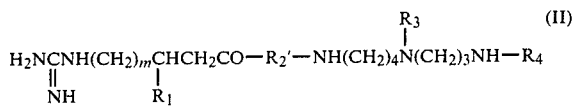

wherein $R_1$ is as defined above, $R_2'$ represents an amino acid residue (except for the residue of α-hydroxyglycine) formed by the removal of one hydrogen atom and hydroxyl group from respectively the α- or ω-amino group and the α-carboxyl group of an α- or ω-amino acid (in case the α- or ω-amino acid has a functional group, the group may be protected), said amino acid residue forming acid amide linkages with the adjacent carbonyl group and amino group, $R_3$ and $R_4$, which may be the same or different, represent protecting groups for the amino groups, and m is an integer of 4 to 6. A detailed description of the invention is given below.

$R_1$ in the general formula (I) is a hydrogen atom, hydroxyl group, or an aliphatic acyloxy group having 1 to 10 carbon atoms such as formyloxy, acetoxy, propionyloxy, butanoyloxy, pentanoyloxy, hexanoyloxy, heptanoyloxy, octanoyloxy, nonanoyloxy, or decanoyloxy group, preferably a lower-acyloxy group having 1 to 4 carbon atoms.

$R_2$ is the residue (except for the residue of α-hydroxyglycine) formed by removing one hydrogen atom and hydroxyl group from respectively the α- or ω-amino group and the carboxyl group of an α- or ω-amino acid (hereinafter such a residue is referred to briefly as amino acid residue). Any amino acid residue, is suitable for $R_2$, so long as it is derived from known α- or ω-amino acid. When an optically active carbon atom is present in the amino acid residue, it may be in any of the configurations L, D and DL.

Examples of amino acid residues represented by $R_2$ are those of the formula

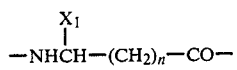

wherein $X_1$ represents a hydrogen atom or a straight chain or branched chain alkyl group of 1 to 6 carbon atoms which may have as substituent a hydroxyl, lower alkoxy, carboxyl, (lower)alkyloxycarbonyl, amino, guanidino, phenyl, hydroxy-substituted phenyl, imidazole, indole, mercapto, or (lower)alkylmercapto group, and n is an integer of 0 to 5, and those of the formula

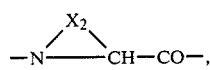

wherein $X_2$ is a propylene group which may have a hydroxyl group as substituent. Examples of individual amino acids corresponding to the above acid residues are α-amino acids including glycine, alanine, α-aminobutyric acid, proline, valine, norvaline, isoleucine, alloisoleucine, leucine, norleucine, serine, homoserine, threonine, allothreonine, O-methylserine, O-ethylserine, O-methylhomoserine, O-ethylhomoserine, O-methylthreonine, O-ethylthreonine, O-methylallothreonine, O-ethylallothreonine, ornithine, lysine, aspartic acid, glutamic acid, asparagine, glutamine, arginine, phenylalanine, tyrosine, histidine, tryptophan, cysteine, homocysteine, S-methylcysteine, S-ethylcysteine, methionine, and ethionine; and other amino acids such as β-alanine, γ-aminobutyric acid, δ-aminovaleric acid, and ε-aminocaproic acid.

In the general formula (I), m is an integer of 4 to 6. When $R_1$ is a group other than hydrogen atom, the configuration of the carbon atom attached to $R_1$ may be S, R, or RS. Among the compounds of formula (I), preferred compounds having a pronounced biological activity are those in which m is 4 or 6 and the amino acid residue is a residue of glycine, serine, β-alanine, γ-aminobutyric acid, arginine or phenylalanine.

As typical examples of the compounds of formula (I), there are the following compounds:

10-[N-(7-guanidinoheptanoyl)-glycyl]-1,5,10-triazadecane
10-[N-(7-guanidino-3-hydroxyheptanoyl)-glycyl]-1,5,10-triazadecane
10-[N-(7-guanidino-3-acetoxyheptanoyl)-glycyl]-1,5,10-triazadecane
10-[N-(7-guanidino-3-propionyloxyheptanoyl)-glycyl]-1,5,10-triazadecane
10-[N-(7-guanidino-3-butanoyloxyheptanoyl)-glycyl]-1,5,10-triazadecane
10-{N-(9-guanidinononanoyl)-glycyl]-1,5,10-triazadecane
10-[N-(9-guanidino-3-hydroxynonanoyl)-glycyl]-1,5,10-triazadecane
10-[N-(7-guanidinoheptanoyl)-L-, D- and DL-seryl]-1,5,10-triazadecane
10-[N-(7-guanidino-3-hydroxyheptanoyl)-L-, D- and DL-seryl]-1,5,10-triazadecane
10-[N-(7-guanidino-3-acetoxyheptanoyl)-L-, D- and DL-seryl]-1,5,10-triazadecane
10-[N-(7-guanidino-3-propionyloxyheptanoyl)-L-, D- and DL-seryl]-1,5,10-triazadecane
10-[N-(7-guanidino-3-butanoyloxyheptanoyl)-L-, D- and DL-seryl]-1,5,10-triazadecane
10-[N-(9-guanidinononanoyl)-L-, D- and DL-seryl]-1,5,10-triazadecane
10-[N-(9-guanidino-3-hydroxynonanoyl)-L-, D- and DL-seryl]-1,5,10-triazadecane
10-[N-(7-guanidinoheptanoyl)-L-, D- and DL-alanyl]-1,5,10-triazadecane
10-[N-(7-guanidino-3-hydroxyheptanoyl)-L-, D- and DL-alanyl]-1,5,10-triazadecane
10-[N-(7-guanidino-3-acetoxyheptanoyl)-L-, D- and DL-alanyl]-1,5,10-triazadecane
10-[N-(7-guanidino-3-propionyloxyheptanoyl)-L-, D- and DL-alanyl]-1,5,10-triazadecane
10-[N-(7-guanidino-3-butanoyloxyheptanoyl)-L-, D- and DL-alanyl]-1,5,10-triazadecane
10-[N-(9-guanidinononanoyl)-L-, D- and DL-alanyl]-1,5,10-triazadecane
10-[N-(9-guanidino-3-hydroxynonanoyl)-L-, D- and DL-alanyl]-1,5,10-triazadecane
10-[N-(7-guanidinoheptanoyl)-β-alanyl]-1,5,10-triazadecane
10-[N-(7-guanidino-3-hydroxyheptanoyl)-β-alanyl]-1,5,10-triazadecane
10-[N-(7-guanidino-3-acetoxyheptanoyl)-β-alanyl]-1,5,10-triazadecane
10-[N-(7-guanidino-3-propionyloxyheptanoyl)-β-alanyl]-1,5,10-triazadecane
10-[N-(7-guanidino-3-butanoyloxyheptanoyl)-β-alanyl]-1,5,10-triazadecane
10-[N-(9-guanidinononanoyl)-β-alanyl]-1,5,10-triazadecane
10-[N-(9-guanidino-3-hydroxynonanoyl)-β-alanyl]-1,5,10-triazadecane
10-[N-(7-guanidinoheptanoyl)-γ-aminobutanoyl]-1,5,10-triazadecane
10-[N-(7-guanidino-3-hydroxyheptanoyl)-γ-aminobutanoyl]-1,5,10-triazadecane
10-[N-(7-guanidino-3-acetoxyheptanoyl)-γ-aminobutanoyl]-1,5,10-triazadecane
10-[N-(7-guanidino-3-propionyloxyheptanoyl)-γ-aminobutanoyl]-1,5,10-triazadecane
10-[N-(7-guanidino-3-butanoyloxyheptanoyl)-γ-aminobutanoyl]-1,5,10-triazadecane
10-[N-(9-guanidinononanoyl)-γ-aminobutanoyl]-1,5,10-triazadecane
10-[N-(9-guanidino-3-hydroxynonanoyl)-γ-aminobutanoyl]-1,5,10-triazadecane
10-[N-(7-guanidinoheptanoyl)-L-, D- and DL-α-aminobutanoyl]-1,5,10-triazadecane
10-[N-(7-guanidino-3-hydroxyheptanoyl)-L-, D- and DL-α-aminobutanoyl]-1,5,10-triazadecane
10-[N-(7-guanidino-3-acetoxyheptanoyl)-L-, D- and DL-α-aminobutanoyl]-1,5,10-triazadecane
10-[N-(9-guanidinononanoyl)-L-, D- and DL-α-aminobutanoyl]-1,5,10-triazadecane
10-[N-(7-guanidinoheptanoyl)-L-, D- and DL-prolyl]-1,5,10-triazadecane
10-[N-(7-guanidino-3-hydroxyheptanoyl)-L-, D- and DL-prolyl]-1,5,10-triazadecane
10-[N-(7-guanidino-3-acetoxyheptanoyl)-L-, D- and DL-prolyl]-1,5,10-triazadecane
10-[N-(9-guanidinonoanoyl)-L-, D- and DL-prolyl]-1,5,10-triazadecane
10-[N-(7-guanidinoheptanoyl)-L-, D- and DL-valyl]-1,5,10-triazadecane
10-[N-(7-guanidino-3-hydroxyheptanoyl)-L-, D- and DL-valyl]-1,5,10-triazadecane
10-[N-(7-guanidino-3-acetoxyheptanoyl)-L-, D- and DL-valyl]-1,5,10-triazadecane
10-[N-(9-guanidinononanoyl)-L-, D- and DL-valyl]-1,5,10-triazadecane
10-[N-(7-guanidinoheptanoyl)-L-, D- and DL-isoleucyl]-1,5,10-triazadecane
10-[N-(7-guanidino-3-hydroxyheptanoyl)-L-, D- and DL-isoleucyl]-1,5,10-triazadecane
10-[N-(7-guanidino-3-acetoxyheptanoyl)-L-, D- and DL-isoleucyl]-1,5,10-triazadecane
10-[N-(9-guanidinononanoyl)-L-, D- and DL-isoleucyl]-1,5,10-triazadecane
10-[N-(7-guanidinoheptanoyl)-L-, D- and DL-leucyl]-1,5,10-triazadecane
10-[N-(7-guanidino-3-hydroxyheptanoyl)-L-, D- and DL-leucyl]-1,5,10-triazadecane
10-[N-(7-guanidino-3-acetoxyheptanoyl)-L-, D- and DL-leucyl]-1,5,10-triazadecane
10-[N-(9-guanidinononanoyl)-L-, D- and DL-leucyl]-1,5,10-triazadecane
10-[N-(7-guanidinoheptanoyl)-L-, D- and DL-homoseryl]-1,5,10-triazadecane
10-[N-(7-guanidino-3-hydroxyheptanoyl)-L-, D- and DL-homoseryl]-1,5,10-triazadecane 10-[N-(7-guanidino-3-acetoxyheptanoyl)-L-, D- and DL-homoseryl]-1,5,10-triazadecane
10-[N-(9-guanidinononanoyl)-L-, D- and DL-homoseryl]-1,5,10-triazadecane
10-[N-(7-guanidinoheptanoyl)-L-, D- and DL-threonyl]-1,5,10-triazadecane
10-[N-(7-guanidino-3-hydroxyheptanoyl)-L-, D- and DL-threonyl]-1,5,10-triazadecane
10-[N-(7-guanidino-3-acetoxyheptanoyl)-L-, D- and DL-threonyl]-1,5,10-triazadecane
10-[N-(9-guanidinononanoyl)-L-, D- and DL-threonyl]-1,5,10-triazadecane
10-[N$^\alpha$-(7-guanidinoheptanoyl)-L-, D- and DL-lysyl]-1,5,10-triazadecane
10-[N$^\alpha$-(7-guanidino-3-hydroxyheptanoyl)-L-, D- and DL-lysyl]-1,5,10-triazadecane
10-[N$^\alpha$-(7-guanidino-3-acetoxyheptanoyl)-L-, D- and DL-lysyl]-1,5,10-triazadecane
10-[N$^\alpha$-(9-guanidinononanoyl)-L-, D- and DL-lysyl]-1,5,10-triazadecane
10-[N-(7-guanidinoheptanoyl)-L-, D- and DL-aspartyl]-1,5,10-triazadecane
10-[N-(7-guanidino-3-hydroxyheptanoyl)-L-, D- and DL-aspartyl]-1,5,10-triazadecane
10-[N-(7-guanidino-3-acetoxyheptanoyl)-L-, D- and DL-aspartyl]-1,5,10-triazadecane
10-[N-(9-guanidinononanoyl)-L-, D- and DL-aspartyl]-1,5,10-triazadecane
10-[N-(7-guanidinoheptanoyl)-L-, D- and DL-glutamyl]-1,5,10-triazadecane
10-[N-(7-guanidino-3-hydroxyheptanoyl)-L-, D- and DL-glutamyl]-1,5,10-triazadecane
10-[N-(7-guanidino-3-acetoxyheptanoyl)-L-, D- and DL-glutamyl]-1,5,10-triazadecane
10-[N-(9-guanidinononanoyl)-L-, D- and DL-glutamyl]-1,5,10-triazadecane
10-[N-(7-guanidinoheptanoyl)-L-, D- and DL-asparaginyl]-1,5,10-triazadecane
10-[N-(7-guanidino-3-hydroxyheptanoyl)-L-, D- and DL-asparaginyl]-1,5,10-triazadecane
10-[N-(7-guanidino-3-acetoxyheptanoyl)-L-, D- and DL-asparaginyl]-1,5,10-triazadecane
10-[N-(9-guanidinononanoyl)-L-, D- and DL-asparaginyl]-1,5,10-triazadecane
10-[N-(7-guanidinoheptanoyl)-L-, D- and DL-glutaminyl]-1,5,10-triazadecane
10-[N-(7-guanidino-3-hydroxyheptanoyl)-L-, D- and DL-glutaminyl]-1,5,10-triazadecane
10-[N-(7-guanidino-3-acetoxyheptanoyl)-L-, D- and DL-glutaminyl]-1,5,10-triazadecane
10-[N-(9-guanidinononanoyl)-L-, D- and DL-glutaminyl]-1,5,10-triazadecane
10-[N$^\alpha$-(7-guanidinoheptanoyl)-L-, D- and DL-arginyl]-1,5,10-triazadecane
10-[N$^\alpha$-(7-guanidino-3-hydroxyheptanoyl)-L-, D- and DL-arginyl]-1,5,10-triazadecane
10-[N$^\alpha$-(7-guanidino-3-acetoxyheptanoyl)-L-, D- and DL-arginyl]-1,5,10-triazadecane
10-[N$^\alpha$-(9-guanidinononanoyl)-L-, D- and DL-arginyl]-1,5,10-triazadecane
10-[N-(7-guanidinoheptanoyl)-L-, D- and DL-phenylalanyl]-1,5,10-triazadecane
10-[N-(7-guanidino-3-hydroxyheptanoyl)-L-, D- and DL-phenylalanyl]-1,5,10-triazadecane
10-[N-(7-guanidino-3-acetoxyheptanoyl)-L-, D- and DL-phenylalanyl]-1,5,10-triazadecane
10-[N-(9-guanidinononanoyl)-L-, D- and DL-phenylalanyl]-1,5,10-triazadecane
10-[N-(7-guanidinoheptanoyl)-L-, D- and DL-tyrosyl]-1,5,10-triazadecane
10-[N-(7-guanidino-3-hydroxyheptanoyl)-L-, D- and DL-tyrosyl]-1,5,10-triazadecane
10-[N-(7-guanidino-3-acetoxyheptanoyl)-L-, D- and DL-tyrosyl]-1,5,10-triazadecane
10-[N-(9-guanidinononanoyl)-L-, D- and DL-tyrosyl]-1,5,10-triazadecane
10-[N$^\alpha$-(7-guanidinoheptanoyl)-L-, D- and DL-histidyl]-1,5,10-triazadecane
10-{[N$^\alpha$-(7-guanidino-3-hydroxyheptanoyl)-L-, D- and DL-histidyl]-1,5,10-triazadecane
10-[N$^\alpha$-(7-guanidino-3-acetoxyheptanoyl)-L-, D- and DL-histidyl]-1,5,10-triazadecane
10-[N$^\alpha$-(9-guanidinononanoyl)-L-, D- and DL-histidyl]-1,5,10-triazadecane
10-[N-(7-guanidinoheptanoyl)-L-, D- and DL-tryptophyl]-1,5,10-triazadecane
10-[N-(7-guanidino-3-hydroxyheptanoyl)-L-, D- and DL-tryptophyl]-1,5,10-triazadecane
10-[N-(7-guanidino-3-acetoxyheptanoyl)-L-, D- and DL-tryptophyl]-1,5,10-triazadecane
10-[N-(9-guanidinononanoyl)-L-, D- and DL-tryptophyl]-1,5,10-triazadecane
10-[N-(7-guanidinoheptanoyl)-L-, D- and DL-cysteinyl]-1,5,10-triazadecane
10-[N-(7-guanidino-3-hydroxyheptanoyl)-L-, D- and DL-cysteinyl]-1,5,10-triazadecane
10-[N-(7-guanidino-3-acetoxyheptanoyl)-L-, D- and DL-cysteinyl]-1,5,10-triazadecane
10-[N-(9-guanidinononanoyl)-L-, D- and DL-cysteinyl]-1,5,10-triazadecane
10-[N-(7-guanidinoheptanoyl)-, D- and DL-homocysteinyl]-1,5,10-triazadecane
10-[N-(7-guanidino-3-hydroxyheptanoyl)-L-, D- and DL-homocysteinyl]-1,5,10-triazadecane
10-[N-(7-guanidino-3-acetoxyheptanoyl)-L-, D- and DL-homocysteinyl]-1,5,10-triazadecane
10-[N-(9-guanidinononanoyl)-L-, D- and DL-homocysteinyl]-1,5,10-triazadecane
10-[N-(7-guanidinoheptanoyl)-L-, D- and DL-methionyl]-1,5,10-triazadecane
10-[N-(7-guanidino-3-hydroxyheptanoyl)-L-, D- and DL-methionyl]-1,5,10-triazadecane
10-[N-(7-guanidino-3-acetoxyheptanoyl)-L-, D- and DL-methionyl]-1,5,10-triazadecane
10-[N-(9-guanidinononanoyl)-L-, D- and DL-methionyl]-1,5,10-triazadecane
10-[N-(7-guanidinoheptanoyl)-L-, D- and DL-O-methylseryl]-1,5,10-triazadecane
10-[N-(7-guanidino-3-hydroxyheptanoyl)-L-, D- and DL-O-methylseryl]-1,5,10-triazadecane
10-[N-(7-guanidino-3-acetoxyheptanoyl)-L-, D- and DL-O-methylseryl]-1,5,10-triazadecane
10-[N-(9-guanidinononanoyl)-L-, D- and DL-O-methylseryl]-1,5,10-triazadecane
10-[N-(7-guanidinoheptanoyl)-L-, D- and DL-S-methylcysteinyl]-1,5,10-triazadecane
10-[N-(7-guanidino-3-hydroxyheptanoyl)-L-, D- and DL-S-methylcysteinyl]-1,5,10-triazadecane
10-[N-(7-guanidino-3-acetoxyheptanoyl)-L-, D- and DL-S-methylcysteinyl]-1,5,10-triazadecane
10-[N-(9-guanidinononanoyl)-L-, D- and DL-S-methylcysteinyl]-1,5,10-triazadecane Compounds of the general formula (I) forms salts with acids. The acids suitable for forming the salts may be either inorganic or organic, so long as the salt is non-toxic. No special restriction is posed upon these inorganic and organic acids, but preferable inorganic acids are hydrochloric acid, sulfuric acid, nitric acid, and phosphoric acid; preferable organic acids are acetic, propionic, succinic, fumaric, maleic, malic, tartaric, glutaric, citric, benzenesulfonic, toluenesulfonic, methanesulfonic, ethanesulfonic, propanesulfonic, aspartic, and glutamic acids.

The present compounds of the general formula (I) are prepared by removing the protecting groups from the compounds of the general formula (II) by a known method such as reduction, hydrolysis, or acid decomposition.

The reaction is usually performed in an inactive solvent at a temperature of $-50°$ to $100°$ C., preferably $-40°$ to $70°$ C. The solvents are for example water, an inactive organic solvent such as lower alcohol (methanol, ethanol, etc.), lower alkyl carboxylic acid (acetic acid, etc.), dioxane, etc. The compound of the formula (I) wherein $R_2$ is a group represented by the general formula

   (b)

wherein $X_1$ and n are as defined previously, is prepared by removing the protecting group from the compound of the formula (II) wherein $R_2'$ is a group represented by the general formula

   (a)

wherein $X_1'$ represents a hydrogen atom or an alkyl group having 1 to 6 carbon atoms, which alkyl group may have as substituent, a hydroxyl, lower alkoxy, carboxyl, (lower)alkyloxycarbonyl, amino, guanidino, phenyl, hydroxy-substituted phenyl, imidazole, mercapto or (lower)alkylmercapt group and a functional group in these substituents may be protected and n is integer of 0 to 5. Typical protecting groups and the methods of their removal are as shown in Table 1, wherein the columns of protecting groups for carboxyl, hydroxyl, mercapto, imidazole, and guanidino groups show the protecting groups and the methods of their removal when $R_2'$ bears said functional groups which are protected with said protecting groups. In Table 1, each protecting group is removable by the method marked with the symbol +, but not by those marked with the symbol −; the method marked with the symbol ± will cause partial removal or decomposition and, hence, is not suitable for the removal of the protecting group.

The protecting groups which can be used in the present method are not limited to those shown in Table 1, but there may be used all of those described in the literature such as, for example, Shiro Akabori, Takeo Kaneko, and Kozo Narita, editors: "Protein Chemistry, I, Amino Acids and Peptides.," Kyoritsu Shuppan, 1969; Nobuo Izumiya, editor: "Peptide Synthesis.," Maruzen, 1975; E. Schröder and K. Lübke: "The Peptides.," Academic Press, New York, 1965; E. Wüsch, "Synthese von Peptiden.," in Houben-Weyl: "Methoden der Organischen Chemie.," Georg Thiem Verlag, Stuttgart, 1974; M. Bodamszky and M. A. Ondetti, "Peptide Synthesis.," Interscience Publishers, New York, 1976.

The protecting groups $R_3$ and $R_4$ are preferably and alkoxycarbonyl group having 1 to 6 carbon atom, a benzyloxycarbonyl group, halogen-substituted benzyloxycarbonyl group, nitro-substituted benzyloxycarbonyl group, (lower)alkoxy-substituted benzyloxycarbonyl group, an acyl group, especially halo(lower)alkylcarbonyl groups or a phtahlyl group.

The suitable method for removing the protecting group varies with the protecting group. Such methods include catalytic reduction in the presence of a noble metal catalyst such as palladium, reduction with metallic sodium or the like, and acid decomposition by using an acid such as hydrogen halide, lower fatty acid (e.g. acetic acid), or a halogeno derivative of lower fatty acids (e.g. trifluoroacetic acid).

The isolation of the compound of formula (I) from the reaction mixture produced by the removal of a protecting group is performed in the following way. For instance, when the protecting group was removed by the catalytic reduction with palladium black as catalyst, the catalyst is removed by filtration and the filtrate is concentrated under reduced pressure. Then the residue is subjected to a known purification method using CM-Sephadex® (Na+) and Sephadex®LH-20 {T. Takeuchi et al., J. Antibiotics, Vol. 34, 1619 (1981)}. When the protective group was removed by use of trifluoroacetic acid, the isolation can be achieved by directly concentrating the reaction mixture under reduced pressure, and subjecting the residue to a known purification method as described above. The above purification method yields a spergualin-related compound of the general formula (I) in the form of hydrochloride. To convert the hydrochloride into other salts, for instance, an aqueous solution of the hydrochloride is passed through a strongly basic ion-exchange resin, the effluents containing the intended product are collected, and neutralized by adding a desired acid or its solution in water or in a hydrophilic organic solvent such as methanol, ethanol, acetone, tetrahydrofuran, or dioxane. The neutralized solution is evaporated to dryness under reduced pressure, or, when the solution contains an organic solvent, the solution is freed from the organic solvent by distillation under reduced pressure, and lyophilized. Alternatively, the conversion of the hydrochloride of the compound of formula (I) into other salts is effected by adding an aqueous silver hydroxide or silver oxide solution to the hydrochloride to neutralize the hydrogen chloride, removing the insoluble silver chloride by filtration, adding to the filtrate a desired acid to form a salt, and lyophilizing the resulting salt. The product obtained forms sometimes a hydrate, depending upon the treating conditions.

The compound of the general formula (II) used as starting material in the method of this invention is a novel compound and can be synthesized by condensing 1,5-diprotected-1,5,10-triazadecane represented by the general formula

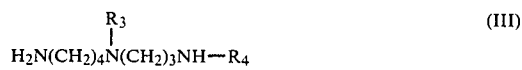   (III)

wherein $R_3$ and $R_4$ are as defined previously, with N-protected α- or ω-amino acid represented by the general formula

   (IV)

wherein $R_5$ is a residue (except for the residue of α-hydroxyglycine) formed by the removal of a hydroxyl group from the α-carboxyl group of α- or ω-amino acid having its amino group protected with a protecting group different from $R_3$ and $R_4$, to obtain 10-[N-(protected)-aminoacyl]-1,5-diprotected-1,5,10-triazadecane represented by the general formula

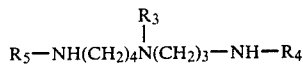 (V)

wherein $R_3$, $R_4$ and $R_5$ are as defined above, then removing from this compound in a customary manner the protecting group for the amino group of the amino acid residue $R_5$ to yield 10-aminoacyl-1,5-diprotected-1,5,10-triazadecane represented by the formula

 (VI)

wherein $R_2'$, $R_3$ and $R_4$ are as defined above, and further reacting the resulting compound with an ω-guanidino-fatty acid represented by the general formula

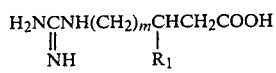 (VII)

wherein $R_1$ and m are as defined above to obtain the compound of the general formula (II). Although not critical, the molar ratio of the compound of formula (VII) to the compound of formula (VI) in the reactant mixture is usually from 0.2 to 5, preferably 0.6 to 1.5.

The condensation of the compound of formula (VI) with the compound of formula (VII) is achieved according to the method customarily used in forming a peptide linkage such as the carbodiimide method employing dicyclohexylcarbodiimide, 1-ethyl-3-(3-dimethylaminopropyl)-carbodiimide, or the like, the azide method by way of a hydrazide, the mixed acid anhydride method employing ethyl chlorocarbonate, isobutyl chlorocarbonate, or the like, the method of active esters such as cyanomethyl ester, vinyl ester, substituted or unsubstituted phenyl ester, thiophenyl ester, hydroxysuccinimide ester, or the like, the O-acylhydroxylamine derivative method using acetoxime, cyclohexanone oxime, or the like, and the N-acyl compound method employing carbonyldiimidazole, or the like. The solvents used in the condensation are those commonly used in the formation of a peptide linkage, which include ethers such as diethyl ether, tetrahydrofuran, and dioxane; esters such as ethyl acetate; ketones such as acetone and methyl ethyl ketone; halogenated hydrocarbons such as methylene chloride and chloroform; amides such as dimethylformamide and dimethylacetamide; and nitriles such as acetonitrile. The reaction temperature is in the range of generally −30° to 60° C., preferably −20° to 30° C.

The 1,5-diprotected-1,5,10-triazadecane of the general formula (III), used as starting material, can be synthesized by condensing in a customary manner monoamino-protected 1,4-butanediamine of the formula

(wherein $R_6$ is an amino-protecting group different from $R_4$ mentioned above) with an amino-protected 3-halogenopropanamine of the formula

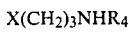 (VIII)

wherein $R_4$ is the same amino-protecting group as mentioned above and X is a halogen atom, to form a compound of the formula

 (IX)

wherein $R_4$ and $R_6$ are amino-protecting groups different from each other, then protecting the remaining imino group with an amino-protecting group represented by $R_3$, which is different from $R_6$ and can be removed by the same method as that for the removal of amino-protecting group $R_4$, and selectively removing the amino-protecting group $R_6$ to yield 1,5-diprotected-1,5,10-triazadecane of the general formula (III).

Another 1,5-diprotected-1,5,10-triazadecane of the formula (III) in which $R_3$ and $R_4$ are the same protecting group is synthesized by reacting 1-(4-aminobutyl)-hexahydropyrimidine of the formula

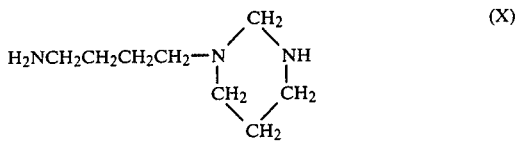 (X)

with N-ethoxycarbonylphthalimide to yield 1-(4-phthalimidobutyl)-hexahydropyrimidine of the formula

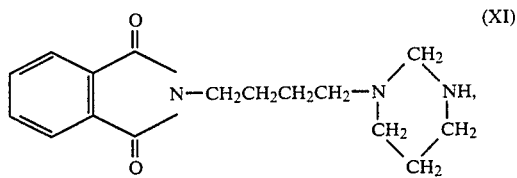 (XI)

then hydrolyzing the resulting compound under acidic conditions to convert it to 10-phthalyl-1,5,10-triazadecane of the formula

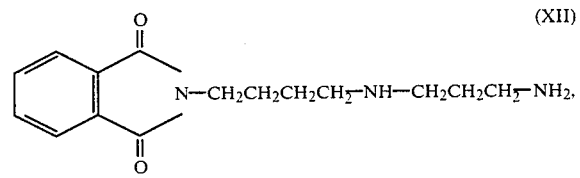 (XII)

then protecting the amino groups in a customary manner to yield 10-phthalyl-1,5-diprotected-1,5,10-triazadecane of the formula

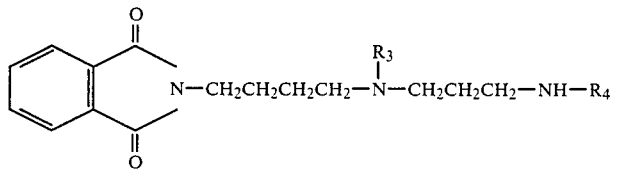

(XIII)

wherein R₃ and R₄ are the same protecting group, and removing the phthalyl group in a customary manner to obtain 1,5-diprotected-1,5,10-triazadecane of the formula (III) in which R₃ and R₄ are the same group. In the above procedure, although any of the amino-protecting groups commonly used in the conventional peptide synthesis can be used, the amino-protecting group $R_6$ must be selectively removable, leaving the amino-propecting groups R₃ and R₄ intact.

The ω-guanidino-fatty acids of the general formula (VII) are synthesized, for example, in the following manner. The compound of the formula (VII) in which $R_1$ is a hydroxyl group and m is 4 is a known compound described in the Journal of Antibiotics, Vol. 36, 1623 (1981), which is obtained by the hydrolysis of spergualin. The compound of formula (VII) in which $R_1$ is an acyloxy group and m is 4 is obtained by acylation of the above compound having a hydroxyl group as $R_1$. Further, when $R_1$ is a hydrogen atom and m is 4 to 6, the compound is identical with the compound disclosed in B.P. No. 1,153,424, which is obtained by converting the corresponding ω-amino acid to a guanidino derivative in a customary manner.

TABLE 1

Protecting Groups for Functional Groups of Amino Acids, and Methods of Removing Them

| | Abbreviation | Removal method | H₂/Pd | Na/NH₃ | HBr/AcOH | HCl | AcOH | CF₃COOH | NH₂NH₂ | NaOH | NH₄OH | HF |
|---|---|---|---|---|---|---|---|---|---|---|---|---|
| | Removing agent | | Hydrogen in the presence of palladium | Metallic sodium | Hydrogen bromide | Hydrogen chloride | Acetic acid | Trifluoro-acetic acid | Hydrazine | Sodium hydroxide | Ammonia | Liquid hydrogen fluoride |
| | Solvent | | Lower alcohol, dimethylform-amide, Acetic acid | Liquid ammonia | Acetic acid | Ethyl acetate, Lower alcohol, Acetic acid, Dioxane | Acetic acid | Trifluoro-acetic acid | Lower alcohol | Water, Lower alcohol | Water, Lower alcohol | Liquid hydrogen fluoride |
| | Temperature | | room temp. to 50° C. | −30° C. or lower | 0° to 50° C. | 0° to room temp. | 0° to b.p. | 0° to room temp. | room temp. to b.p. | 0° to 50° C. | 0° to 50° C. | 20° C. or lower |
| | Pressure | | atmospheric pressure to 100 kg/cm² | atmospheric pressure | atmospheric pressure | atmospheric pressure | atmospheric pressure | atmospheric pressure | atmospheric pressure | atmospheric pressure | atmospheric pressure | atmospheric pressure |
| Amino protecting group | C₆H₅OCO— | | + | + | + | + | − | ± | − | − | − | + |
| | (CH₃)₃COCO— | | − | − | + | + | ± | + | − | − | − | + |
| | (C₆H₅)₃C— | | + | + | ± | + | + | + | − | − | − | − |
| | CH₃—⟨C₆H₄⟩—SO₂— | | − | + | − | − | − | − | − | − | − | − |
| | HCO— | | − | ± | − | ± | − | − | − | − | − | − |
| | ⟨phthaloyl⟩ | | − | + | − | + | − | − | + | ± | ± | − |
| | CF₃CO— | | + | + | + | + | − | − | ± | + | + | − |
| | CH₃O—C₆H₄—CH₂OCO— | | + | + | + | + | − | − | − | − | − | + |
| | R—C₆H₄—CH₂OCO— | | + | + | + | + | − | + | − | − | − | |
| | C₆H₅CH₂— | | − | + | + | − | − | − | − | − | − | |
| | CH₂—CH₂, CH₂—CH₂ CHOCO— | | + | + | + | − | − | − | − | − | − | |
| | (C₆H₅)₂CHOCO— | | + | + | + | + | + | + | − | − | − | + |

TABLE 1-continued

Protecting Groups for Functional Groups of Amino Acids, and Methods of Removing Them

| Abbreviation | H₂/Pd | Na/NH₃ | HBr/AcOH | HCl | AcOH | CF₃COOH | NH₂NH₂ | NaOH | NH₄OH | HF |
|---|---|---|---|---|---|---|---|---|---|---|
| 2-NO₂-C₆H₄-S— | | | + | + | | + | | | | + |
| Carboxyl-protecting group | | | | | | | | | | |
| (C₆H₅)₃C—S—(CH₃)₂CHOCO— | — | — | ± | + | — | — | — | — | ± | + |
| Lower alkyl | — | ± | — | — | ± | — | — | + | — | — |
| (CH₃)₃C— | — | ± | + | ± | — | + | — | ± | — | + |
| C₆H₅CH₂— | + | ± | ± | ± | — | ± | — | + | — | + |
| 4-CH₃O-C₆H₄-CH₂— | + | + | + | + | — | + | | + | | ± |
| 4-NO₂-C₆H₄-CH₂— | ± | — | + | — | — | + | + | + | + | + |
| (C₆H₅)₂CH—(CH₃)₂CH— | — | — | ± | ± | — | ± | + | ± | — | — |
| phthalimide (CO-N-CH₂-CO) | — | + | + | — | | — | — | + | — | |
| Hydroxyl-protecting group | | | | | | | | | | |
| CH₃CO—C₆H₅CO— (phenolic)(CH₃)₃C—C₆H₅CH₂— | — | + | | | + | | | — | | |
| 4-CH₃-C₆H₄-SO₂— (phenolic) | + | ± | + | + | | + | | + | | |
| tetrahydropyranyl | + | — | ± | ± | | + | | — | — | + |
| Mercapto- | | | | | | | | | | |
| C₆H₅CH₂OCO— (phenolic)(C₆H₅)₃C—C₆H₅CH₂— | | | | | | | | — | — | + |

TABLE 1-continued

Protecting Groups for Functional Groups of Amino Acids, and Methods of Removing Them

| | Abbreviation | H₂/Pd | Na/NH₃ | HBr/AcOH | HCl | AcOH | CF₃COOH | NH₂NH₂ | NaOH | NH₄OH | HF |
|---|---|---|---|---|---|---|---|---|---|---|---|
| protecting group | (C₆H₅)₃C— | | | + | + | | + | | | | + |
| | C₆H₅CH₂OCO— | | — | + | — | | — | | | | ± |
| | (CH₃)₃C— | | + | ± | — | | ± | | | | + |
| | (C₆H₅)₂CH— | | | — | — | | — | | | | — |
| | C₆H₅CO— | | | | | | | | + | | + |
| | CH₃O—⟨⟩—CH₂— | + | + | + | + | | + | | | | |
| | O₂N—⟨⟩—CH₂— | ± | + | — | — | | + | | + | | + |
| | | | + | + | | | — | | — | | |
| Nitrogen protecting group for imidazole | C₆H₅CH₂OCO— | + | ± | + | — | | + | — | — | | + |
| | C₆H₅CH₂— | | | | | | | | | | |
| | (C₆H₅)₃C— | | | | | | | | | | |
| Guanidino-protecting group | NO₂— | — | + | — | — | | — | — | — | | |
| | CH₃—⟨⟩—SO₂— | | + | + | | | | | + | | + |
| | NO₂—⟨⟩—CH₂OCO— | | — | + | + | — | + | | — | | + |
| | (CH₃)₃COCO— | | | | | | | | | | |

Note: 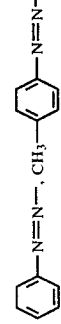

R = Cl, Br, NO₂, 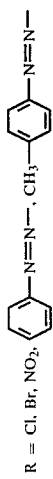

The compounds of the general formula (II) can also be synthesized by condensing acid salts of ω-guanidinoacylamino acids of the general formula (XIV)

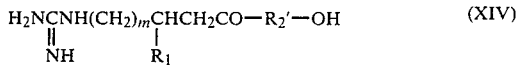

wherein $R_1$, $R'_2$ and m are as defined previously, with protected 1,5,10-triazadecanes of the general formula (III)

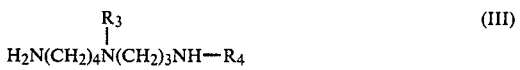

wherein $R_3$ and $R_4$ are as defined previously. The ω-guanidinoacylamino acids of the general formual (XIV) are novel compounds, and can be obtained by condensing acid salts of the ω-guanidino fatty acids of the general formual (VII) with α- or ω-amino acids of the general formula (XV)

wherein $R_2'$ is as defined above, and $R_7$ represents a protecting group for the α-carboxyl group of the α- or ω-amino acid, or a hydrogen atom, to form acid salts of ω-guanidinoacylamino acids of the general formula (XVI)

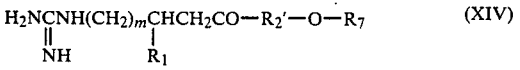

wherein m, $R_1$, $R_2'$ and $R_7$ are as defined above, and if $R_7$ is the protecting group, further removing it by common methods. The condensation reaction between the ω-guanidinoacylamino acids of the general formula (XIV) and the protected 1,5,10-triazadecanes of the general formual (III) can be carried out in the same way as for the condensation between the compounds of the general formual (VI) and the compounds of the general formual (VII).

Typical examples of the protected spergualin-related compounds of the general formula (II) are listed below:
10-[N-(7-guanidinoheptanoyl)-glycyl]-1,5-dibenzyloxycarbonyl-1,5,10-triazadecane
10-[N-(7-guanidinoheptanoyl)-glycyl]-1,5-di-tert-butoxycarbonyl-1,5,10-triazadecane
10-[N-(7-guanidino-3-hydroxyheptanoyl)-glycyl]-1,5-dibenzyloxycarbonyl-1,5,10-triazadecane
10-[N-(7-guanidino-3-hydroxyheptanoyl)-glycyl]-1,5-di-tert-butoxycarbonyl-1,5,10-triazadecane
10-[N-(7-guanidino-3-acetoxyheptanoyl)-glycyl]-1,5-dibenzyloxycarbonyl-1,5,10-triazadecane
10-[N-(7-guanidino-3-acetoxyheptanoyl)-glydyl]-1,5-di-tert-butoxycarbonyl-1,5,10-triazadecane
10-[N-(7-guanidino-3-propionyloxyheptanoyl)-glydyl]-1,5-dibenzyloxycarbonyl-1,5,10-triazadecane
10-[N-(7-guanidino-3-propionyloxyheptanoyl)-glycyl]-1,5-di-tert-butoxycarbonyl-1,5,10-triazadecane
10-[N-(7-guanidino-3-butanoyloxyheptanoyl)-glycyl]-1,5-dibenzyloxycarbonyl-1,5,10-triazadecane
10-[N-(7-guanidino-3-butanoyloxyheptanoyl)-glycyl]-1,5-di-tert-butoxycarbonyl-1,5,10-triazadecane
10-[N-(9-guanidinononanoyl)-glycyl]-1,5-dibenzyloxycarbonyl-1,5,10-triazadecane
10-[N-(9-guanidinononanoyl)-glydyl]-1,5,-di-tert-butoxycarbonyl-1,5,10-triazadecane
10-[N-(9-guanidino-3-hydroxynonanoyl)-glycyl]-1,5-dibenzyloxycarbonyl-1,5,10-triazadecane
10-[N-(9-guanidino-3-hydroxynonanonyl)-glycyl]-1,5-di-tert-butoxycarbonyl-1,5,10-triazadecane
10-[N-(7-guanidinoheptanoyl)-L-, D- and DL-seryl]-1,5-dibenzyloxycarbonyl-1,5,10-triazadecane
10-[N-(7-guanidinoheptanoyl)-L-, D- and DL-seryl]-1,5-di-tert-butoxycarbonyl-1,5,10-triazadecane
10-[N-(7-guanidinoheptanoyl)-O-benzyl-L-, D- and DL-seryl]-1,5-dibenzyloxycarbonyl-1,5,10-triazadecane
10-[N-(7-guanidinoheptanoyl)-O-tert-butyl-L-, D- and DL-seryl]-1,5-di-tert-butoxycarbonyl-1,5,10-triazadecane
10-[N-(7-guanidino-3-hydroxyheptanoyl)-L-, D- and DL-seryl]-1,5,-dibenzyloxycarbonyl-1,5,10-triazadecane
10-[N-(7-guanidino-3-hydroxyheptanoyl)-L-, D- and DL-seryl]-1,5-di-tert-butoxycarbonyl-1,5,10-triazadecane
10-[N-(7-guanidino-3-hydroxyheptanoyl)-O-benzyl-L-, D- and DL-seryl]-1,5-dibenzyloxycarbonyl-1,5,10-triazadecane
10-[N-(7-guanidino-3-hydroxyheptanoyl)-O-tert-butyl-L-, D- and DL-seryl]-1,5,-di-tert-butoxycarbonyl-1,5,10-triazadecane
10-[N-(7-guanidino-3-acetoxyheptanoyl)-L-, D- and DL-seryl]-1,5,-dibenzyloxycarbonyl-1,5,10-triazadecane
10-[N-(7-guanidino-3-acetoxyheptanoyl)-L-, D- and DL-seryl]-1,5-di-tert-butoxycarbonyl-1,5,10-triazadecane
10-[N-(7-guanidino-3-acetoxyheptanoyl)-O-benzyl-L-, D- and DL-seryl]-1,5-dibenzyloxycarbonyl-1,5,10-triazadecane
10-[N-(7-guanidino-3-acetoxyheptanoyl)-O-tert-butyl-L-, D- and DL-seryl]-1,5,di-tert-butoxycarbonyl-1,5,10-triazadecane
10-[N-(7-guanidino-3-propionyloxyheptanoyl)-L-, D- and DL-seryl]-1,5,-dibenzyloxycarbonyl-1,5,10-triazadecane
10-[N-(7-guanidino-3-propionyloxyheptanoyl)-L-, D- and DL-seryl]-1,5-di-tert-butoxycarbonyl-1,5,10-triazadecane
10-[N-(7-guanidino-3-propionyloxyheptanoyl)-O-benzyl-L-, D- and DL-seryl]-1,5-dibenzyloxycarbonyl-1,5,10-triazadecane
10-[N-(7-guanidino-3-propionyloxyheptanoyl)-O-tert-butyl-L-, D- and DL-seryl]-1,5-di-tert-butoxycarbonyl-1,5,10-triazadecane
10-[N-(7-guanidino-3-butanoyloxyheptanoyl)-L-, D- and DL-seryl]-1,5-dibenzyloxycarbonyl-1,5,10-triazadecane
10-[N-(7-guanidino-3-butanoyloxyheptanoyl)-L-, D- and DL-seryl]-1,5-di-tert-butoxycarbonyl-1,5,10-triazadecane
10-[N-(7-guanidino-3-butanoyloxyheptanoyl)-O-benzyl-L-, D- and DL-seryl]-1,5-dibenzyloxycarbonyl-1,5,10-triazadecane
10-[N-(7-guanidino-3-butanoyloxyheptanoyl)-O-tert-butyl-L-, D- and DL-seryl]-1,5-di-tert-butoxycarbonyl-1,5,10-triazadecane
10-[N-(9-guanidinononanoyl)-L-, D- and DL-seryl]-1,5-dibenzyloxycarbonyl-1,5,10-triazadecane 10-[N-(9-guanidinononanoyl)-L-, D- and DL-seryl]-1,5-di-tert-butoxycarbonyl-1,5,10-triazadecane 10-[N-(9-guanidinononanoyl)-O-benzyl-L-, D- and DL-seryl]-1,5-dibenzyloxycarbonyl-1,5,10-triazadecane 10-[N-(9-guanidinononanoyl)-O-tert-butyl-L-, D- and DL-seryl]-1,5-di-tert-butoxycarbonyl-1,5,10-triazadecane 10-[N-(9-guanidino-3-hydroxynonanoyl)-L-, D- and DL-seryl]-1,5-dibenzyloxycarbonyl-1,5,10-triazadecane 10-[N-(9-guanidino-3-hydroxynonanoyl)-O-benzyl-L-, D- and DL-seryl]-1,5-dibenzyloxycarbonyl-1,5,10-triazadecane 10-[N-(7-guanidinoheptanoyl)-L-, D- and DL-alanyl]-1,5-dibenzyloxycarbonyl-1,5,10-triazadecane 10-[N-(9-guanidinononanoyl)-L-, D- and DL-alanyl]-1,5-dibenzyloxycarbonyl-1,5,10-triazadecane 10-[N-(7-guanidinoheptanoyl)-$\beta$-alanyl]-1,5-dibenzyloxycarbonyl-1,5,10-triazadecane 10-[N-(7-guanidinoheptanoyl)-$\beta$-alanyl]-1,5-di-tert-butoxycarbonyl-1,5,10-triazadecane 10-[N-(7-guanidino-3-hydroxyheptanoyl)-$\beta$-alanyl]-1,5-dibenzyloxycarbonyl-1,5,10-triazadecane 10-[N-(7-guanidino-3-hydroxyheptanoyl)-$\beta$-alanyl]-1,5-di-tert-butoxycarbonyl-1,5,10-triazadecane 10-[N-(7-guanidino-3-acetoxyheptanoyl)-$\beta$-alanyl]-1,5-dibenzyloxycarbonyl-1,5,10-triazadecane 10-[N-(7-guanidino-3-acetoxyheptanoyl)-$\beta$-alanyl]-1,5-di-tert-butoxycarbonyl-1,5,10-triazadecane 10-[N-(7-guanidino-3-propionyloxyheptanoyl)-$\beta$-alanyl]-1,5-dibenzyloxycarbonyl-1,5,10-triazadecane 10-[N-(7-guanidino-3-butanoyloxyheptanoyl)-$\beta$-alanyl]-1,5-dibenzyloxycarbonyl-1,5,10-triazadecane 10-[N-(9-guanidinononanoyl)-$\beta$-alanyl]-1,5-dibenzyloxycarbonyl-1,5,10-triazadecane 10-[N-(9-guanidinononanoyl)-$\beta$-alanyl]-1,5,-di-tert-butoxycarbonyl-1,5,10-triazadecane 10-[N-9-guanidino-3-hydroxynonanoyl)-$\beta$-alanyl]-1,5-dibenzyloxycarbonyl-1,5,10-triazadecane 10-[N-(9-guanidino-3-hydroxynonanoyl)-$\beta$-alanyl]-1,5-di-tert-butoxycarbonyl-1,5,10-triazadecane 10-[N-(7-guanidinoheptanoyl)-$\gamma$-aminobutanoyl]-1,5-dibenzyloxycarbonyl-1,5,10-triazadecane 10-[N-(7-guanidino-3-hydroxyheptanoyl)-$\gamma$-aminobutanoyl]-1,5-dibenzyloxycarbonyl-1,5,10-triazadecane 10-[N-(7-guanidinoheptanoyl)-L-, D- and DL-$\alpha$-aminobutanoyl]-1,5-dibenzyloxycarbonyl-1,5,10-triazadecane 10-[N-(7-guanidinoheptanoyl)-L-, D- and DL-prolyl]-1,5-dibenzyloxycarbonyl-1,5,10-triazadecane 10-[N-(7-guanidinoheptanoyl)-L-, D- and DL-valyl]-1,5-dibenzyloxycarbonyl-1,5,10-triazadecane 10-[N-(7-guanidinoheptanoyl)-L-, D- and DL-isoleucyl]-1,5-dibenzyloxycarbonyl-1,5,10-triazadecane 10-[N-(7-guanidinoheptanoyl)-L-, D- and DL-leucyl]-1,5-dibenzyloxycarbonyl-1,5,10-triazadecane 10-[N-(7-guanidino-3-hydroxyheptanoyl)-L-, D- and DL-leucyl]-1,5-dibenzyloxycarbonyl-1,5,10-triazadecane 10-[N-(7-guanidinoheptanoyl)-L-, D- and DL-homoseryl]-1,5-dibenzyloxycarbonyl-1,5,10-triazadecane 10-[N-(7-guanidinoheptanoyl)-L-, D- and DL-homoseryl]-1,5-di-tert-butoxycarbonyl-1,5,10-triazadecane 10-[N-(9-guanidinononanoyl)-L-, D- and DL-homoseryl]-1,5-dibenzyloxycarbonyl-1,5,10-triazadecane 10-[N-(7-guanidinoheptanoyl)-L-, D- and DL-threonyl]-1,5-dibenzyloxycarbonyl-1,5,10-triazadecane 10-[N-(7-guanidino-3-hydroxyheptanoyl)-L-, D- and DL-threonyl]-1,5-dibenzyloxycarbonyl-1,5,10-triazadecane 10-[N-(9-guanidinononanoyl)-L-, D- and DL-threonyl]-1,5-dibenzyloxycarbonyl-1,5,10-triazadecane 10-[N$^\alpha$-(7-guanidinoheptanoyl)-N$^\epsilon$-benzyloxycarbonyl-L-, D- and DL-lysyl]-1,5-dibenzyloxycarbonyl-1,5,10-triazadecane 10-[N-(7-guanidinoheptanoyl)-$\beta$-benzyl-L-, D- and DL-aspartyl]-1,5-dibenzyloxycarbonyl-1,5,10-triazadecane 10-[N-(7-guanidino-3-hydroxyheptanoyl)-L-, D- and DL-aspartyl]-1,5-dibenzyloxycarbonyl-1,5,10-triazadecane 10-[N-(9-guanidinononanoyl)-L-, D- and DL-aspartyl]-1,5-dibenzyloxycarbonyl-1,5,10-triazadecane 10-[N-(7-guanidinoheptanoyl)-L-, D- and DL-glutamyl]-1,5-dibenzyloxycarbonyl-1,5,10-triazadecane 10-[N-(7-guanidino-3-hydroxyheptanoyl)-L-, D- and DL-glutamyl]-1,5-dibenzyloxycarbonyl-1,5,10-triazadecane 10-[N-(9-guanidinononanoyl)-L-, D- and DL-glutamyl]-1,5-dibenzyloxycarbonyl-1,5,10-triazadecane 10-[N-(7-guanidinoheptanoyl)-L-, D- and DL-asparaginyl]-1,5-dibenzyloxycarbonyl-1,5,10-triazadecane 10-[N-9-guanidinononanoyl)-L-, D- and DL-asparaginyl]-1,5-dibenzyloxycarbonyl-1,5,10-triazadecane 10-[N-(7-guanidinoheptanoyl)-L-, D- and DL-glutaminyl]-1,5-dibenzyloxycarbonyl-1,5,10-triazadecane 10-[N$^\alpha$-(7-guanidinoheptanoyl)-L-, D- and DL-arginyl]-1,5-dibenzyloxycarbonyl-1,5,10-triazadecane 10-[N$^\alpha$-(7-guanidinoheptanoyl)-L-, D- and DL-arginyl]-1,5-di-tert-butoxycarbonyl-1,5,10-triazadecane 10-[N$^\alpha$-(7-guanidinoheptanoyl)-N$^g$-nitro-L-, D- and DL-arginyl]-1,5-dibenzyloxycarbonyl-1,5,10-triazadecane 10-[N$^\alpha$-(7-guanidino-3-hydroxyheptanoyl)-L-, D- and DL-arginyl]-1,5-dibenzyloxycarbonyl-1,5,10-triazadecane 10-[N-(7-guanidinoheptanoyl)-L-, D- and DL-phenylalanyl]-1,5-dibenzyloxycarbonyl-1,5,10-triazadecane 10-[N-(7-guanidinoheptanoyl)-L-, D- and DL-phenylalanyl]1,5-di-tert-butoxycarbonyl-1,5,10-triazadecane 10-[N-(7-guanidino-3-hydroxyheptanoyl)-L-, D- and DL-phenylalanyl]-1,5-dibenzyloxycarbonyl-1,5,10-triazadecane 10-[N-(7-guanidino-3-acetoxyheptanoyl)-L-, D- and DL-phnylalanyl]-1,5-dibenzyloxycarbonyl-1,5,10-triazadecane 10-[N-(9-guanidinononanoyl)-L-, D- and DL-phenylalanyl]-1,5-dibenzyloxycarbonyl-1,5,10-triazadecane 10-[N-(7-guanidinoheptanoyl)-L-, D- and DL-tyrosyl]-1,5-dibenzyloxycarbonyl-1,5,10-triazadecane 10-[Nα-(7-guanidinoheptanoyl)-N^{im}-benzoyloxycarbonyl-L-, D- and DL-histidyl]-1,5-dibenzyloxycarbonyl-1,5,10-triazadecane 10-[N-(7-guanidinoheptanoyl)-L-, D- and DL-tryptophyl]-1,5-dibenzyloxycarbonyl-1,5,10-triazadecane 10-[N-(7-guanidinoheptanoyl)-L-, D- and DL-cysteinyl]-1,5-dibenzyloxycarbonyl-1,5,10-triazadecane 10-[N-(7-guanidinoheptanoyl)-S-p-methoxybenzyl-L-, D- and DL-cysteinyl]-1,5-dibenzyloxycarbonyl-1,5,10-triazadecane 10-[N-(7-guanidinoheptanoyl)-L-, D- and DL-homocysteinyl]-1,5-dibenzyloxycarbonyl-1,5,10-triazadecane 10-[N-(7-guanidinoheptanoyl)-S-benzyl-L-, D- and DL-homocysteinyl]-1,5-dibenzyloxycarbonyl-1,5,10-triazadecane 10-[N-(7-guanidinoheptanoyl)-L-, D- and DL-methionyl]-1,5-dibenzyloxycarbonyl-1,5,10-triazadecane 10-[N-(7-guanidinoheptanoyl)-L-, D- and DL-O-methylseryl]1,5-dibenzyloxycarbonyl-1,5,10-triazadecane 10-[N-(7-guanidino-3-hydroxyheptanoyl)-L-, D- and DL-O-methylseryl]-1,5-dibenzyloxycarbonyl-1,5,10-triazadecane 10-[N-(9-guanidinononanoyl)-L-, D- and DL-O-methylseryl]1,5-dibenzyloxycarbonyl-1,5,10-triazadecane 10-[N-(7-guanidinoheptanoyl)-L-, D- and DL-S-methylcysteinyl]-1,5-dibenzyloxycarbonyl-1,5,10-triazadecane 10-[N-(9-guanidinononaoyl)-L-, D- and DL-S-methylcysteinyl]1,5-di-tert-butoxycarbonyl-1,5,10-triazadecane Experiments were conducted on the compounds of this invention to investigate their stability in aqueous solutions, their inhibitory action on the growth of Bacillus subtilis, their in vitro inhibitory action on the proliferation of mouse leukemia L1210 cells, and their in vivo action on the prolongation of life and their toxicity in mice receiving the same cells by transplantation. Table 2 shows the compounds of this invention that were used in these tests.

TABLE 2

$$H_2N\underset{\underset{NH}{\|}}{C}NH(CH_2)_m CHCH_2CO-R_2-NH(CH_2)_4NH(CH_2)_3NH_2$$
$$\phantom{H_2NCNH(CH_2)_m CH}\underset{R_1}{|}$$

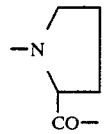

| Compd. No. | m | R₁ | R₂ | | (amino acid residue) |
|---|---|---|---|---|---|
| 1 | 4 | H | —NH—CH₂—CO— | (L) | (glycyl) |
| 2 | 4 | H | —NH—CH(CH₂OH)—CO— | (L) | (L-seryl) |
| 3 | 4 | (S) OH | " | (") | (L-seryl) |
| 4 | 4 | H | " | (D) | (D-seryl) |
| 5 | 4 | H | —NH—CH(CH₃)—CO— | (L) | (L-alanyl) |
| 6 | 4 | H | —NH—CH₂CH₂—CO | | (β-alanyl) |
| 7 | 4 | H | —NH—CH₂CH₂CH₂—CO— | | (γ-aminobutanoyl) |
| 8 | 4 | H | —N(pyrrolidine)—CO— | (L) | (L-prolyl) |
| 9 | 4 | H | —NH—CH(CH₂CH(CH₃)₂)—CO— | (L) | (L-leucyl) |
| 10 | 4 | H | —NH—CH(CH₂COOH)—CO— | (L) | (aspartyl) |
| 11 | 4 | H | —NH—CH(CH₂CH₂COOH)—CO— | (L) | (L-glutamyl) |
| 12 | 4 | H | —NH—CH(CH₂CH₂CH₂NH—C(=NH)—NH₂)—CO— | (L) | (L-arginyl) |
| 13 | 4 | H | —NH—CH(CH₂—C₆H₅)—CO— | (L) | (L-phenylalanyl) |

TABLE 2-continued $$H_2NCNH(CH_2)_mCHCH_2CO-R_2-NH(CH_2)_4NH(CH_2)_3NH_2$$
$$\underset{NH}{\|} \quad \underset{R_1}{|}$$

| Compd. No. | m | $R_1$ | $R_2$ | | (amino acid residue) |
|---|---|---|---|---|---|
| 14 | 4 | H | -NH-CH-CO- with CH$_2$-imidazole side chain | (L) | (L-histidyl) |
| 15 | 4 | H | -NH-CH-CO- with CHOH-CH$_3$ side chain | (L) | (L-threonyl) |
| 16 | 4 | (S)-OCOCH$_3$ | -NH-CH$_2$-CO- | | (glycyl) |
| 17 | 6 | H | -NH-CH-CO- with CH$_2$OH side chain | (L) | (L-seryl) |
| 18 | 4 | H | -NH-CH-CO- with CH$_2$CH$_2$OH side chain | (DL) | (DL-homoseryl) |

1. Stability of the compounds of this invention in aqueous solutions (1) Testing method Each of the compounds of this invention was dissolved in water to a concentration of 0.5 (w/w)%. The aqueous solution was maintained at 40°±1° C., and sampled at certain time intervals. Each sample was subjected to high-performance liquid chromatographic analysis to measure the area of the peak of the compound at each sampling time, and to calculate the ratio of the area of the peak after the indicated period of time to that at the first sampling time. The results of the calculation were used to determine the contents (%) of the compound of this invention in the aqueous solution after the indicated periods of time, with the initial content of said compound set at 100%.

(2) Test results

Table 3 gives the results of the above test.

TABLE 3

Residual content (%) of the compound of this invention in an aqueous solution

| Comp. No. | Time (hr) that elapsed | | | | | | |
|---|---|---|---|---|---|---|---|
| | 0 | 12 | 24 | 48 | 72 | 120 | 168 |
| 1 | 100 | 99.7 | 100 | 99.7 | 99.7 | 99.8 | 99.9 |
| 2 | " | 100 | 100 | 99.8 | 100 | 99.7 | 99.8 |
| 3 | " | 99.3 | 99.5 | 100 | 99.6 | 99.7 | 100 |
| 4 | " | 101 | 100 | 100 | 99.7 | 99.6 | 100 |
| 5 | " | 99.8 | 99.8 | 100 | 99.6 | 99.0 | 99.9 |
| 6 | " | 100 | 100 | 99.6 | 99.6 | 99.9 | 100 |
| 7 | " | 99.9 | 100 | 99.8 | 99.9 | 100 | 99.8 |
| 8 | " | 100 | 100 | 99.6 | 99.8 | 99.8 | 100 |
| 9 | " | 99.7 | 99.9 | 99.8 | 100 | 100 | 99.9 |
| 10 | " | 99.9 | 99.4 | 99.8 | 100 | 99.8 | 99.9 |
| 11 | " | 99.5 | 99.7 | 101 | 99.5 | 100 | 99.3 |
| 12 | " | 100 | 99.4 | 99.7 | 99.9 | 100 | 99.7 |
| 13 | " | 99.8 | 99.5 | 99.9 | 100 | 101 | 100 |
| 14 | " | 99.1 | 99.0 | 99.6 | 99.5 | 99.9 | 99.6 |
| 15 | " | 99.2 | 99.8 | 99.1 | 100.2 | 99.6 | 100.1 |
| 16 | " | 99.9 | 99.5 | 99.6 | 99.2 | 99.6 | 99.6 |
| 17 | " | 99.6 | 100.2 | 99.8 | 99.7 | 100 | 99.3 |
| 18 | " | 100 | 99.5 | 99.7 | 99.3 | 99.7 | 99.5 |
| Spergualin | " | 94.6 | 90.8 | 84.6 | 78.5 | 69.9 | 65.1 |

2. Growth-inhibiting action of the compounds of this invention on *Bacilus subtilis*

(1) Testing method

Each of the compounds of this invention was dissolved in nutrient agar media to final concentrations of 100, 50, 25, 12.5, 6.25, 3.13 and 1.56 μg/ml, to prepare agar plates for testing. *Bacillus subtilis* PCI219 was adjusted to a content of 1 × 10⁶ viable cells/ml, in a culture broth, and a loopful of the broth was applied onto the agar plates. The plates were incubated for 20 hours at 37° C. under stationary conditions, and observed for the formation of colonies of *Bacillus subtilis*. The lowest of the concentrations at which no colonies were formed was taken to be minimum inhibitory concentration (MIC).

(2) Test results

Table 4 shows the growth-inhibiting action of typical examples of the compounds of this invention on *Bacillus subtilis*. The intensity of this action is expressed by MIC.

TABLE 4

Growth-inhibiting action of the compounds of this invention on *Bacillus subtilis*

| Compound (Example No.) | MIC (μg/ml) |
|---|---|
| 1 | 6.25 |
| 2 | 12.5 |
| 3 | 6.25 |
| 4 | 12.5 |
| 5 | 25.0 |
| 6 | 25.0 |
| 7 | 25.0 |
| 8 | >100 |
| 9 | >100 |
| 10 | >100 |
| 11 | >100 |
| 12 | 12.5 |
| 13 | >100 |
| 14 | 50.0 |
| 15 | 100 |
| 16 | >100 |
| 17 | 6.25 |
| 18 | 100 |

3. In vitro proliferation-inhibiting action of the compounds of this invention on mouse leukemia L1210 cells (1) Testing method Leukemia L1210 cells (1×10⁵/0.2 ml) were transplanted to female DBA/2 mice intraperitoneally. four days later, the ascitic fluid was collected and centrifuged to obtain proliferated L1210 cells. The L1210 cells collected were added to RPMI1640 medium containing bovine fetal serum and 2-mercaptoethanol, to obtain a suspension of L1210 cells having a final concentration of $5 \times 10^4$ cells/0.9 ml. Each of the compounds of this invention was dissolved in said culture medium to prepare solutions with final concentrations ranging from 0.062 to 100 μg/ml. 0.9 ml of the L1210 cell suspension and 0.1 ml of each test solution were mixed in petri dishes, and incubated for 48 hours at 37° C. in an incubator under an atmosphere of carbon dioxide gas. The number of L1210 cells was counted before and after the incubation, and that concentration of the compound which inhibited the proliferation of L1210 cells by 50% of the control's proliferation was determined ($IC_{50}$).

(2) Test results

Table 5 shows the proliferation-inhibiting action of typical examples of the compounds of this invention on mouse leukemia L1210 cells. The intensity of the action is expressed by the value of $IC_{50}$.

TABLE 5

| In vitro proliferation-inhibiting action of compounds of this invention on mouse leukemia L1210 cells | |
|---|---|
| Compound (Example No.) | $IC_{50}$ (μg/ml) |
| 1 | 1.7 |
| 2 | 4.5 |
| 3 | 0.95 |
| 4 | 3.6 |
| 5 | 37 |
| 6 | 0.84 |
| 7 | 1.9 |
| 9 | 70 |
| 10 | 130 |
| 12 | 1.5 |
| 13 | 2.8 |
| 14 | 51 |
| 15 | 180 |
| 17 | 11.3 |
| 18 | 150 |
| Spergualin | 4.6 |

4. Life-prolonging effect and toxicity of the compounds of this invention in mouse leukemia L1210

(1) Testing method

Leukemia L1210 cells (1×10⁵/0.2 ml) were transplanted intraperitoneally into male CDF₁-SLC mice (6 mice/group). Each of the compounds of this invention was diluted with physiological saline to various concentrations. Each dilution was administered at a dose of 0.1 ml/10 g of body weight once daily for 9 days, starting on the day after the day of the transplantation. The mice of the control group were administered physiological saline.

The mice were observed for 60 days, beginning on the day after the day of L1210 transplantation, to examine how many days each mouse survived. The average number of days that the group receiving the compound of this invention survived was calculated. The FIGURE obtained was divided by the average number of survival days for the control group, and was multiplied by 100 (T/C (%)). T/C value more than 125 was considered to be effective.

Change in body weight, the measure of the toxicity of the compounds of this invention, was expressed by a difference between the change in body weight for the group receiving the compound of this invention and that for the control group receiving physiological saline and undergoing no transplantation.

(2) Test results

Table 6 shows the life-prolonging effect of typical examples of the compounds of this invention on moust leukemia L1210, and their toxicity. The life-prolonging effect is expressed by T/C, and the toxicity by the change in body weight.

TABLE 6

| Life-prolonging effect of the compounds of this invention on mouse leukemia L1210, and their toxicity | | | |
|---|---|---|---|
| Compound (Example No.) | Dose (mg/kg/day) | T/C (%) | Change in body weight (g) |
| Control | 0.00 | 100 | 1.8 |
| 1 | 50.00 | 12.9 | — |
|  | 25.00 | >279 | −1.6 |
|  | 12.50 | >528 | +0.2 |
|  | 6.25 | >769 | +0.9 |
|  | 3.13 | >667 | +0.8 |
|  | 1.56 | >388 | +1.0 |
|  | 0.78 | >250 | +2.7 |
|  | 0.39 | 126 | +1.8 |
| 2 | 50.00 | 12.8 | — |
|  | 25.00 | 100 | — |
|  | 12.50 | >612 | −0.2 |
|  | 6.25 | >705 | +1.0 |
|  | 3.13 | >769 | +0.6 |
|  | 1.56 | >769 | +1.3 |
|  | 0.78 | >346 | +1.5 |
|  | 0.39 | 124 | +2.7 |
| Spergualin | 50.00 | >342 | +0.2 |
|  | 25.00 | >524 | +1.1 |
|  | 12.50 | >700 | +0.8 |
|  | 6.25 | >769 | +0.9 |
|  | 3.13 | >665 | +1.2 |
|  | 1.56 | >224 | +2.5 |
|  | 0.78 | 129 | +0.8 |

As clear from the above experimental examples, the compounds of this invention have good biological activities, high stability, and are promising as pharmaceuticals such as antitumor agents. Of these compounds represented by the general formula (I), those in which m stands for 4 to 6, $R_1$ represents a hydrogen atom or a hydroxyl group, and the amino acid residue as $R_2$ is glycyl, seryl, β-alanyl, γ-aminobutanoyl, arginyl or phenylalanyl are preferred because of their better activities.

The present invention will be described in more detail with reference to Examples. In the Example, Rf value in thin-layer chromatography (TLC) was determined by applying a solution of the desired product onto a silica gel 60 $F_{254}$ plate (0.25 mm thickness, Merck) at a certain position (so-called origin), developing this plate with the indicated developer over a distance of about 8 cm, and dividing the distance from the origin to the center of the appearing spot for the desired product by the distance from the origin to the forward end of the development zone (so-called solvent front). The desired product was detected by using UV (2537 Å), ninhydrin and Sakaguchi reagent.

EXAMPLE 1

10-[N-(7-guanidinoheptanoyl)-glycyl]-1,5,10-triazadecane trihydrochloride 20.8 grams (24.0 mmols equivalent) of 10-[N-(7-guanidinoheptanoyl)-glycyl]-1,5-dibenzyloxycarbonyl-1,5,10-triazadecane hydrochloride, an oily substance, was dissolved in a mixture of 300 ml of methanol and 10 ml of acetic acid. 0.50 g of palladium black was added to the solution, and the mixture was catalytically reduced for 3 hours at room temperature at atmospheric pressure. After the reaction, the catalyst was removed by filtration, and the filtrate was concentrated under reduced pressure to obtain 19.5 g of oily matter. The oily matter was dissolved in 70 ml of distilled water, and the solution was passed through a column packed with 1500 ml of CM-Sephadex®C-25 (Na+). Gradient elution was made between 7500 ml of distilled water and 7500 ml of an aqueous solution of 1M sodium chloride.

Active fractions were collected, and concentrated to dryness under reduced pressure. Methanol was added to the residue, and the insoluble sodim chloride was removed by filtration. This purification step was repeated two times. To remove a small amount of sodium chloride remained, the resulting oily matter was dissolved in 50 ml of methanol, and the solution was passed through a column packed with 400 ml of Sephadex®LH-20. The column was eluted with methanol, and active fractions were collected, followed by concentrating them under reduced pressure to obtain 5.30 g of an oily substance. The oily substance was dissolved in 20 ml of distilled water, and the insolubles were removed by filtration. The filtrate was freeze-dried to obtain 5.20 g of the desired product in a yield of 45.1%.

mp: 163°–165° C.

NMR (DMSO-$d_6$): $\delta$=0.9–1.8 (b, 12H), 1.8–2.4 (b, 4H) 2.6–3.3 (b, 10H), 3.63 (d, 2H, J=5 Hz) 6.9–9.2 (b, 12H).

IR (KBr): $\nu(cm^{-1})$=3410, 3310, 3150, 2930, 1640, 1520, 1470, 1410, 1160, 965.

TLC (n-propanol:pyridine:water:acetic acid=6:4:3:2 v/v) Rf=0.4.

MS (FD): m/z 372 (M+1).

EXAMPLE 2

10-[N-(7-guanidinoheptanoyl)-L-seryl]-1,5,10-triazadecane trihydrochloride 2.50 g (2.65 mmols equivalent) of 10-[N-(7-guanidinoheptanoyl)-O-benzyl-L-seryl]-1,5-dibenzyloxycarbonyl-1,5,10-triazadecane hydrochloride was dissolved in a mixture of 30 ml methanol and 1 ml of acetic acid. 0.1 g of palladium black was added to the solution, and the mixture was catalytically reduced for 5 hours at atmospheric pressure with heating at 50° C. After the reaction, the catalyst was removed by filtration, and the filtrate was concentrated under reduced pressure to obtain 1.7 g of an oily matter.

The oily matter was dissolved in 6 ml of distilled water, and the solution was chromatographed on a column packed with 300 ml of CM-Sephadex®C-25 (Na+). The column was eluted by gradient elution between 2000 ml of distilled water and 2000 ml of an aqueous solution of 1.5M sodium chloride.

Active fractions were collected, and dried under reduced pressure. Methanol was added to the residue, and the insoluble sodium chloride was removed by filtration. This purification step was performed again. To remove a small amount of sodium chloride remained, the resulting oily material was dissolved in 5 ml of methanol, and the solution was passed through a column packed with 100 ml of Sephadex®LH-20. The column was eluted with methanol, active fractions were collected, and the collected fractions were concentrated under reduced pressure. The resulting oily matter was dissolved in 5 ml of distilled water, and the insolubles were removed by filtration. The filtrate was freeze-dried to obtain 0.50 g of the desired product in a yield of 36.6%.

NMR (DMSO-$d_6$): $\delta$=0.8–1.8 (b, 12H), 1.8–2.4 (b, 4H) 2.5–3.4 (b, 10H), 3.57 (d, 2H, J=5 Hz), 4.18 (m, 1H), 5.5–6.5 (b, 1H), 6.7–9.5 (b, 12H).

IR (KBr): $\nu(cm^{-1})$=3350, 2940, 1640, 1535, 1465, 1375, 1160, 1060, 965.

TLC (n-propanol:pyridine:water:acetic acid=6:4:3:2 (v/v), Rf=0.3.

$[\alpha]_D^{27}$: $-15.2°$ (c=1.0, $H_2O$)

MS (FD): m/z 402 (M+1).

The desired compound was also obtained by the similar procedure to this example using 10-[N-(7-guanidinohepanoyl)-L-seryl]-1,5-dibenzyloxycarbonyl-1,5,10-triazadecane hydrochloride instead of 10-[N-(7-guanidinoheptanoyl)-O-benzyl-L-seryl]-1,5-dibenzyloxycarbonyl-1,5,10-triazadecane hydrochloride as the starting material.

10-[N-(7-guanidinoheptanoyl)-L-seryl]-1,5-dibenzyloxycarbonyl-1,5,10-triazadecane hydrochloride was prepared by using N-tert-butoxycarbonyl-L-serine N-hydroxysuccinimide ester in place of N-tert-butoxycarbonyl-O-benzyl-L-serine N-hydroxysuccinimide ester in Referential Example 2.

EXAMPLES 3–17

The compounds of the general formula (II) shown in the following tables were treated in a similar manner to the procedure of Example 1 or 2 to obtain the compounds of the general formula (I) tabulated below.

| Example | Compound of formula (II) | Compound of formula (I) |
|---|---|---|
| 3 | 10-[N—(7-guanidino-3(S)—hydroxy-heptanoyl)-O—benzyl-L-seryl]-1,5-dibenzyloxycarbonyl-1,5,10-triazadecane hydrochloride<br><br>NMR (DMSO-$d_6$)<br>$\delta$ = 0.9–2.0 (b, 12H)<br>2.1–2.4 (d, 2H, J=6 Hz)<br>2.6–3.5 (b, 10H)<br>3.60 (d, 2H, J=5 Hz)<br>3.8–4.7 (b, 2H)<br>4.48 (s, 2H)<br>4.5–5.5 (b, 1H)<br>5.01 (s, 2H)<br>5.05 (s, 2H)<br>6.7–8.3 (b, 8H)<br>7.27 (s, 5H) | 10-[N—(7-guanidino-3(S)—hydroxy-heptanoyl)-L-seryl]-1,5,10-triazadecane trihydrochloride<br><br>NMR (DMSO-$d_6$)<br>$\delta$ = 1.0–1.8 (b, 10H)<br>1.8–2.4 (b, 4H)<br>2.6–3.5 (b, 10H)<br>3.60 (d, 2H, J=5 Hz)<br>3.7–4.3 (b, 2H)<br>4.3–5.5 (b, 2H)<br>6.9–9.1 (b, 12H)<br><br>IR (KBr)<br>$\nu(cm^{-1})$ = 3365, 2945, 1650, 1540, 1460, 1170, 1060, 965 |

-continued

| Example | Compound of formula (II) | Compound of formula (I) |
|---|---|---|
| | 7.30 (s, 10H)<br>TLC (n-butanol:water:acetic acid = 4:1:1 v/v)<br>Rf = 0.6 | TLC (n-butanol:pyridine:water: acetic acid = 6:4:3:2 v/v)<br>Rf = 0.3<br>$[\alpha]_D^{23}$ −14.7° (c = 1.0, H$_2$O)<br>MS (FD) m/z 418 (M+1) |
| 4 | 10-[N—(7-guanidinoheptanoyl)-O—benzyl-D-seryl]-1,5-dibenzyloxycarbonyl-1,5,10-triazadecane hydrochloride<br>NMR (DMSO-d$_6$)<br>δ = 0.9–2.0 (b, 14H)<br>2.0–2.4 (b, 2H)<br>2.7–3.5 (b, 10H)<br>3.58 (d, 2H, J=5 Hz)<br>4.2–4.8 (b, 1H)<br>4.47 (s, 2H)<br>5.01 (s, 2H)<br>5.04 (s, 2H)<br>6.7–8.3 (b, 8H)<br>7.27 (s, 5H)<br>7.30 (s, 10H)<br>TLC (chloroform:methanol:acetic acid = 9:1:0.5 v/v)<br>Rf = 0.2 | 10-[N—(7-guanidinoheptanoyl)-D-seryl]-1,5,10-triazadecane trihydrochloride<br><br>NMR (DMSO-d$_6$)<br>δ = 0.8–1.9 (b, 12H)<br>1.8–2.4 (b, 4H)<br>2.6–3.4 (b, 10H)<br>3.58 (d, 2H, J=5 Hz)<br>4.18 (m, 1H)<br>5.0–5.8 (b, 1H)<br>6.7–9.4 (b, 12H)<br>IR (KBr)<br>$\nu$(cm$^{-1}$) = 3350, 2940, 1640, 1535, 1460, 1360, 1160, 1060<br>TLC (n-butanol:pyridine:water: acetic acid = 6:4:3:2 v/v)<br>Rf = 0.4<br>$[\alpha]_D^{26}$ +15.3° (c = 1.0, H$_2$O)<br>MS (FD) m/z 402 (M+1) |
| 5 | 10-[N—(7-guanidinoheptanoyl)-L-alanyl]-1,5-dibenzyloxycarbonyl-1,5,10-triazadecane hydrochloride<br>NMR (DMSO-d$_6$)<br>δ = 0.9–2.0 (b, 17H)<br>2.0–2.3 (b, 2H)<br>2.3–3.5 (b, 10H)<br>4.0–4.5 (b, 1H)<br>4.99 (s, 2H)<br>5.03 (s, 2H)<br>6.3–8.7 (b, 8H)<br>7.3 (s, 10H)<br>TLC (n-propanol:pyridine:water: acetic acid = 6:4:3:2 v/v)<br>Rf = 0.8 | 10-[N—(7-guanidinoheptanoyl)-L-alanyl]-1,5,10-triazadecane trihydrochloride<br>NMR (DMSO-d$_6$)<br>δ = 0.9–1.8 (b, 15H)<br>1.8–2.4 (b, 4H)<br>2.6–3.4 (b, 10H)<br>3.9–4.5 (b, 1H)<br>5.9–8.2 (b, 12H)<br>IR (KBr)<br>$\nu$(cm$^{-1}$) = 3380, 2940, 1640, 1540, 1370, 1160, 965<br>TLC (n-propanol:pyridine:water: acetic acid = 6:4:3:2 v/v)<br>Rf = 0.4<br>$[\alpha]_D^{27}$ −21.6° (c = 1.2, H$_2$O)<br>MS (FD) m/z 386 (M+1) |
| 6 | 10-[N—(7-guanidinoheptanoyl)-β-alanyl]-1,5-dibenzyloxycarbonyl-1,5,10-triazadecane hydrochloride<br>NMR (DMSO-d$_6$)<br>δ = 1.0–2.1 (b, 14H)<br>2.0–2.5 (b, 4H)<br>2.6–3.1 (b, 12H)<br>4.99 (s, 2H)<br>5.03 (s, 2H)<br>6.7–8.3 (b, 8H)<br>7.3 (s, 10H)<br>TLC (chloroform:methanol:29% ammonia water = 2:2:1 v/v)<br>Rf = 0.8 | 10-[N—(7-guanidinoheptanoyl)-β-alanyl]-1,5,10-triazadecane trihydrochloride<br>NMR (DMSO-d$_6$)<br>δ = 1.0–1.8 (b, 12H)<br>1.9–2.5 (b, 6H)<br>2.6–3.5 (b, 12H)<br>7.0–9.3 (b, 12H)<br>IR (KBr)<br>$\nu$(cm$^{-1}$) = 3350, 2935, 1635, 1545, 1460, 1365, 1165, 965<br>TLC (chloroform:methanol:29% ammonia water = 2:2:1 v/v)<br>Rf = 0.6<br>MS (FD) m/z 386 (M+1) |
| 7 | 10-[N—(7-guanidinoheptanoyl)-γ-aminobutanoyl]-1,5-dibenzyloxycarbonyl-1,5,10-triazadecane hydrochloride<br>NMR (DMSO-d$_6$)<br>δ = 0.9–2.0 (b, 16H)<br>2.0–2.5 (b, 4H)<br>2.7–3.7 (b, 12H)<br>4.99 (s, 2H)<br>5.03 (s, 2H)<br>6.5–8.5 (b, 8H)<br>7.30 (s, 10H)<br>TLC (n-butanol:water:acetic acid = 4:1:1 v/v)<br>Rf = 0.6 | 10-[N—(7-guanidinoheptanoyl)-γ-aminobutanoyl]-1,5,10-triazadecane trihydrochloride<br>NMR (DMSO-d$_6$)<br>δ = 0.9–1.8 (b, 14H)<br>1.8–2.4 (b, 6H)<br>2.6–3.4 (b, 12H)<br>6.7–9.2 (b, 12H)<br>IR (KBr)<br>$\nu$(cm$^{-1}$) = 3350, 2940, 1640, 1550, 1460, 1360<br>TLC (n-propanol:pyridine:water: acetic acid = 6:4:3:2 v/v)<br>Rf = 0.4<br>MS (FD) m/z 400 (M+1) |
| 8 | 10-[N—(7-guanidinoheptanoyl)-L-prolyl]-1,5-dibenzyloxycarbonyl-1,5,10-triazadecane hydrochloride | 10-[N—(7-guanidinoheptanoyl)-L-prolyl]-1,5,10-triazadecane trihydrochloride |

| Example | Compound of formula (II) | Compound of formula (I) |
|---|---|---|
| | NMR (DMSO-d$_6$) <br> $\delta$ = 0.9–2.4 (b, 20H) <br> 2.7–3.7 (b, 12H) <br> 4.0–4.4 (b, 1H) <br> 5.00 (s, 2H) <br> 5.04 (s, 2H) <br> 6.5–7.9 (b, 7H) <br> 7.33 (s, 10H) <br> TLC (n-butanol:acetic acid:water = 4:1:1 v/v) <br> Rf = 0.3 | NMR (DMSO-d$_6$) <br> $\delta$ = 1.0–2.4 (b, 20H) <br> 2.5–3.9 (b, 12H) <br> 4.0–4.5 (b, 1H) <br> 6.7–9.3 (b, 11H) <br> IR (KBr) <br> $\nu$(cm$^{-1}$) = 3400, 2940, 1640, 1450, 1160, 965 <br> TLC (n-propanol:pyridine:water: acetic acid = 6:4:3:2 v/v) <br> Rf = 0.3 <br> $[\alpha]_D^{27}$ −42.3° (c = 1.3, H$_2$O) <br> MS (FD) m/z 412 (M+1) |
| 9 | 10-[N—(7-guanidinoheptanoyl)-L-leucyl]-1,5-dibenzyloxycarbonyl-1,5,10-triazadecane hydrocholoride <br> NMR (DMSO-d$_6$) <br> $\delta$ = 0.6–1.0 (b, 6H) <br> 1.1–1.9 (b, 16H) <br> 1.9–2.4 (b, 3H) <br> 2.7–3.5 (b, 10H) <br> 3.8–4.6 (m, 1H) <br> 5.06 (s, 2H) <br> 5.10 (s, 2H) <br> 6.8–8.3 (b, 8H) <br> 7.33 (s, 10H) <br> TLC (n-butanol:water:acetic acid = 4:1:1 v/v) <br> Rf = 0.5 | 10-[N—(7-guanidinoheptanoyl)-L-leucyl]-1,5,10-triazadecane trihydrochloride <br> NMR (DMSO-d$_6$) <br> $\delta$ = 0.5–1.0 (b, 6H) <br> 1.0–1.9 (b, 15H) <br> 1.9–2.3 (b, 4H) <br> 2.6–3.5 (b, 10H) <br> 3.9–4.5 (b, 1H) <br> 6.8–9.1 (b, 12H) <br> IR (KBr) <br> $\nu$(cm$^{-1}$) = 3400, 2945, 1645, 1535, 1465, 1370, 1165, 970 <br> TLC (n-propanol:pyridine:water: acetic acid = 6:4:3:2 v/v) <br> Rf = 0.4 <br> $[\alpha]_D^{27}$ −20.5° (c = 1.4, H$_2$O) <br> MS (FD) m/z 428 (M+1) |
| 10 | 10-[N—(7-guanidinoheptanoyl)-$\beta$-benzyl-L-aspartyl]-1,5-dibenzyloxycarbonyl-1,5,10-triazadecane hydrochloride <br> NMR (DMSO-d$_6$) <br> $\delta$ = 1.0–2.5 (b, 14H) <br> 1.9–2.4 (b, 2H) <br> 2.4–3.7 (b, 12H) <br> 4.3–4.9 (b, 1H) <br> 5.00 (s, 2H) <br> 5.05 (s, 4H) <br> 5.2–6.4 (b, 3H) <br> 6.7–8.0 (b, 5H) <br> 7.33 (s, 15H) <br> TLC (n-butanol:water:acetic acid = 4:4:1 v/v) <br> Rf = 0.4 | 10-[N—(7-guanidinoheptanoyl)-L-asparthyl]-1,5,10-triazadecane trihydrochloride <br> NMR (DMSO-d$_6$) <br> $\delta$ = 0.9–1.8 (b, 12H) <br> 1.8–2.6 (b, 6H) <br> 2.7–3.5 (b, 10H) <br> 4.1–4.7 (b, 1H) <br> 6.9–8.7 (b, 13H) <br> IR (KBr) <br> $\nu$(cm$^{-1}$) = 3320, 2935, 1640, 1550, 1470, 1390, 1310, 1170, 965 <br> TLC (n-butanol:pyridine:water: acetic acid = 6:4:3:2 v/v) <br> Rf = 0.4 <br> $[\alpha]_D^{27}$ −10.3° (c = 1.5, H$_2$O) <br> MS (FD) m/z 430 (M+1) |
| 11 | 10-[N—(7-guanidinoheptanoyl)-L-glutaminyl]-1,5-dibenzyloxycarbonyl-1,5,10-triazadecane hydrochloride <br> NMR (DMSO-d$_6$) <br> $\delta$ = 0.9–2.4 (b, 20H) <br> 2.6–3.8 (b, 10H) <br> 3.9–4.3 (b, 1H) <br> 4.99 (s, 2H) <br> 5.04 (s, 2H) <br> 6.5–8.3 (b, 10H) <br> 7.34 (s, 10H) <br> TLC (chloroform:methanol:acetic acid = 8:2:0.5 v/v) <br> Rf = 0.1 | 10-[N—(7-guanidinoheptanoyl)-L-glutaminyl]-1,5,10-triazadecane trihydrochloride <br> NMR (DMSO-d$_6$) <br> $\delta$ = 0.8–1.8 (b, 14H) <br> 1.8–2.4 (b, 6H) <br> 2.6–3.8 (b, 12H) <br> 4.0–4.3 (m, 1H) <br> 6.5–9.2 (b, 12H) <br> IR (KBr) <br> $\nu$(cm$^{-1}$) = 3400, 2940, 1655, 1540, 1455, 1160, 965 <br> TLC (n-propanol:pyridine:water: acetic acid = 6:4:3:2 v/v) <br> Rf = 0.4 <br> $[\alpha]_D^{23}$ −11.2° (c = 1.1, H$_2$O) <br> MS (FD) m/z 443 (M+1) |
| 12 | 10-[N—(7-guanidinoheptanoyl)-N$^g$—nitro-L-arginyl]-1,5-dibenzyloxycarbonyl-1,5,10-triazadecane hydrochloride <br> NMR (DMSO-d$_6$) <br> $\delta$ = 1.0–1.9 (b, 18H) <br> 1.9–2.5 (b, 2H) <br> 2.7–3.8 (b, 12H) <br> 4.1–4.5 (b, 1H) <br> 5.01 (s, 2H) | 10-[N—(7-guanidinoheptanoyl)-L-arginyl]-1,5,10-triazadecane trihydrochloride <br> NMR (DMSO-d$_6$) <br> $\delta$ = 1.0–1.9 (b, 16H) <br> 1.9–2.3 (b, 4H) <br> 2.7–3.8 (b, 12H) <br> 4.0–4.5 (b, 1H) <br> 6.5–9.2 (b, 17H) |

-continued

| Example | Compound of formula (II) | Compound of formula (I) |
|---|---|---|
| | 5.04 (s, 2H)<br>6.0–8.4 (b, 11H)<br>7.30 (s, 10H)<br>TLC (n-propanol:pyridine:water:<br>acetic acid = 6:4:3:2 v/v)<br>Rf = 0.8 | IR (KBr)<br>ν(cm$^{-1}$) = 3330, 2930, 1640, 1530,<br>  1460, 1365, 1250, 1160,<br>  1100<br>TLC (n-propanol:pyridine:water:<br>acetic acid = 6:4:3:2 v/v)<br>Rf = 0.2<br>$[\alpha]_D^{23}$ −7.2° (c = 1.2, H$_2$O)<br>MS (FD) m/z 471 (M+1) |
| 13 | 10-[N—(7-guanidinoheptanoyl)-L-<br>phenylalanyl]-1,5-<br>dibenzyloxycarbonyl-1,5,10-<br>triazadecane hydrochloride<br>NMR (DMSO-d$_6$)<br>δ = 0.9–2.4 (b, 16H)<br>  2.7–3.7 (b, 10H)<br>  3.5 (s, 2H)<br>  4.3–4.7 (b, 1H)<br>  4.98 (s, 2H)<br>  5.02 (s, 2H)<br>  6.9–8.3 (b, 8H)<br>  7.17 (s, 5H)<br>  7.30 (s, 10H)<br>TLC (n-butanol:water:acetic acid =<br>4:1:1 v/v)<br>Rf = 0.5 | 10-[N—(7-guanidinoheptanoyl)-L-<br>phenylalanyl]-1,5,10-triazadecane<br>trihydrochloride<br>NMR (DMSO-d$_6$)<br>δ = 0.9–1.8 (b, 12H)<br>  1.9–2.5 (b, 4H)<br>  2.7–3.5 (b, 12H)<br>  4.2–4.7 (b, 1H)<br>  6.9–9.3 (b, 12H)<br>  7.22 (s, 5H)<br>IR (KBr)<br>ν(cm$^{-1}$) = 3320, 2930, 1645, 1530,<br>  1455, 1370, 965, 700<br>TLC (n-propanol:pyridine:water:<br>acetic acid = 6:4:3:2 v/v)<br>Rf = 0.4<br>$[\alpha]_D^{27}$ +6.7° (c = 1.2, H$_2$O)<br>MS (FD) m/z 462 (M+1) |
| 14 | 10-[N—(7-guanidinoheptanoyl)-N$^{im}$—<br>benzyloxycarbonyl-L-histidyl]-1,5-<br>dibenzyloxycarbonyl-1,5,10-<br>triazadecane hydrochloride<br>NMR (DMSO-d$_6$)<br>δ = 0.9–2.0 (b, 14H)<br>  2.0–3.5 (b, 14H)<br>  4.0–4.5 (b, 1H)<br>  4.99 (s, 2H)<br>  5.03 (s, 2H)<br>  5.10 (s, 2H)<br>  6.7–8.0 (b, 12H)<br>  7.31 (s, 15H)<br>TLC (n-butanol:water:acetic acid =<br>4:1:1 v/v)<br>Rf = 0.4 | 10-[N—(7-guanidinoheptanoyl)-L-<br>histidyl]-1,5,10-triazadecane<br>trihydrochloride<br>NMR (DMSO-d$_6$)<br>δ = 0.9–1.8 (b, 12H)<br>  1.8–2.3 (b, 4H)<br>  2.7–3.5 (b, 12H)<br>  4.3–4.9 (b, 1H)<br>  6.3–9.0 (b, 17H)<br>IR (KBr)<br>ν(cm$^{-1}$) = 3370, 2940, 1650, 1540,<br>  1640, 1460, 1370, 1165,<br>  1080<br>TLC (n-propanol:pyridine:water:<br>acetic acid = 6:4:3:2 v/v)<br>Rf = 0.3<br>$[\alpha]_D^{27}$ −2.8° (c = 1.2, H$_2$O)<br>MS (FD) m/z 452 (M+1) |
| 15 | 10-[N—(7-guanidinoheptanoyl)-O—<br>benzyl-L-threonyl]-1,5-<br>dibenzyloxycarbonyl-1,5,10-<br>triazadecane hydrochloride<br>NMR (DMSO-d$_6$)<br>δ = 0.6–2.4 (b, 19H)<br>  2.6–3.5 (b, 10H)<br>  3.5–4.3 (b, 2H)<br>  4.3–4.6 (b, 2H)<br>  4.6–5.2 (b, 3H)<br>  4.98 (s, 2H)<br>  5.02 (s, 2H)<br>  6.5–8.0 (b, 5H)<br>  7.2 (s, 5H)<br>  7.3 (s, 10H)<br>TLC (n-butanol:water:acetic acid =<br>4:4:1 v/v)<br>Rf = 0.7 | 10-[N—(7-guanidinoheptanoyl)-L-<br>threonyl]-1,5,10-triazadecane<br>trihydrochloride<br>NMR (DMSO-d$_6$)<br>δ = 1.05 (d, 3H, J=6 Hz)<br>  0.8–1.9 (b, 12H)<br>  1.9–2.4 (b, 4H)<br>  2.6–4.3 (b, 15H)<br>  6.5–9.5 (b, 10H)<br>IR (KBr)<br>ν(cm$^{-1}$) = 3330, 2940, 1650, 1530,<br>  1465, 1380, 1160, 1110,<br>  930<br>TLC (n-butanol:pyridine:water:<br>acetic acid = 6:4:3:2 v/v)<br>Rf = 0.2<br>$[\alpha]_D^{22}$ −13.1° (c = 1.1, H$_2$O)<br>MS (FD) m/z 416 (M+1) |
| 16 | 10-[N—(7-guanidino-3(S)—<br>acetoxyheptanoyl)-glycyl]-1,5-<br>dibenzloxycarbonyl-1,5,10-<br>triazadecane hydrochloride<br>NMR (DMSO-d$_6$)<br>δ = 0.9–1.9 (b, 12H)<br>  2.0 (s, 3H)<br>  2.2–2.7 (b, 2H)<br>  2.7–3.8 (b, 12H)<br>  4.9–5.3 (b, 1H)<br>  4.98 (s, 2H) | 10-[N—(7-guanidino-3(S)—<br>acetoxyheptanoyl)-glycyl-1,5,10-<br>triazadecane trihydrochloride<br>NMR (DMSO-d$_6$)<br>δ = 1.0–1.8 (b, 10H)<br>  1.8–2.2 (b, 2H)<br>  2.0 (s, 3H)<br>  2.2–2.7 (b, 2H)<br>  2.7–3.5 (b, 10H)<br>  3.65 (b, 2H, J=5 Hz) |

-continued

| Example | Compound of formula (II) | Compound of formula (I) |
|---|---|---|
|  | 5.02 (s, 2H)<br>5.7–9.0 (b, 8H)<br>7.3 (s, 10H) | 4.9–5.3 (b, 1H)<br>5.7–9.6 (b, 12H)<br>IR (KBr)<br>$\nu(cm^{-1})$ = 3390, 2950, 1720, 1650,<br>1545, 1455, 1380, 1250,<br>1170, 1030 |
|  | TLC (n-butanol:water:acetic acid = 4:1:1 v/v)<br>Rf = 0.8 | TLC (n-propanol:pyridine:water:acetic acid = 6:4:3:2 v/v)<br>Rf = 0.27<br>$[\alpha]_D^{20.6}$ −1.4° (c = 1.1, H$_2$O)<br>MS (FD) m/z 417 (M+1) |
| 17 | 10-[N—(9-guanidinononanoyl)-O—benzyl-L-seryl]-1,5-benzyloxycarbonyl-1,5,10-triazadecane<br>NMR (DMSO-d$_6$)<br>$\delta$ = 1.0–2.0 (b, 18H)<br>2.0–2.4 (b, 2H)<br>2.7–3.5 (b, 10H)<br>3.58 (d, 2H, J=6 Hz)<br>4.2–4.8 (b, 1H)<br>4.47 (s, 2H)<br>5.01 (s, 2H)<br>5.05 (s, 2H)<br>6.9–8.3 (b, 8H)<br>7.29 (s, 5H)<br>7.33 (s, 10H) | 10-[N—(9-guanidinononanoyl)-L-seryl]-1,5,10-triazadecane trihydrochloride<br>NMR (DMSO-d$_6$)<br>$\delta$ = 1.0–1.8 (b, 16H)<br>1.8–2.4 (b, 4H)<br>2.6–3.5 (b, 11H)<br>3.55 (d, 2H, J=5 Hz)<br>4.0–4.3 (b, 1H)<br>7.0–9.6 (b, 12H)<br>IR (KBr)<br>$\nu(cm^{-1})$ = 3350, 2940, 1655, 1540,<br>1470, 1160, 1060 |
|  | TLC (chloroform:methanol:acetic acid = 9:1:0.3 v/v)<br>Rf = 0.2 | TLC (n-propanol:pyridine:water:acetic acid = 6:4:3:2 v/v)<br>Rf = 0.6<br>$[\alpha]_D^{25}$ −5.0° (c = 0.5, H$_2$O)<br>MS (FD) m/z 430 (M+1) |

EXAMPLE 18

1.04 g (1.54 mmols) of 10-[N-(7-guanidinoheptanoyl)-DL-homoseryl]-1,5-di-tert-butoxycarbonyl-1,5,10-triazadecane acetate was dissolved, while being cooled, in 3 ml of trifluoroacetic acid. Then, the solution was stirred for 5 hours at room temperature to carry out the elimination of the tert-butoxycarbonyl group. After the reaction, the trifluoroacetic acid was distilled off by concentration under reduced pressure. To the residue was added 10 ml of 1N hydrochloric acid, and the mixture was concentrated under reduced pressure to obtain 0.97 g of oily matter. The oily matter was dissolved in 10 ml of distilled water, and the solution was chromatographed on a column (230 ml) of CM-Sephadex ®C-25 (Na+). The column was eluted using a gradient elution between 1200 ml of distilled water and 1200 ml of an aqueous solution of 0.9M sodium chloride. Active fractions were collected, and concentrated under reduced pressure. Methanol was added to the redidue, and the insoluble sodium chloride was removed by filtration. This purification step was performed again. To remove a small amount of sodium chloride remained, the resulting oily matter was dissolved in 5 ml of methanol, and passed through a column (100 ml) of Sephadex ®LH-20. The column was eluted wih methanol, and active fractions were collected and concentrated under reduced pressure to obtain 0.38 g of an oily substance. This oily substance was dissolved in 4 ml of distilled water, and the insolubles were removed by filtration. The filtrate was freeze-dried to obtain 0.37 g of the desired product in a yield of 45%.

NMR (DMSO-d$_6$): $\delta$=0.6–2.0 (b, 14H), 2.0–2.3 (b, 4H), 2.6–4.0 (b, 15H), 4.0–4.7 (b, 1H) 6.0–9.5 (b, 10H).

IR (KBr): $\nu(cm^{-1})$=3380, 2940, 1650, 1530, 1470, 1380, 1165, 1055, 965.

TLC (n-propanol:pyridine:water:acetic acid=6:4:3:2 v/v), Rf=0.4.

MS (FD): m/z 416 (M+1).

REFERENTIAL EXAMPLE 1

(1)

10-(N,N-phthalylglycyl)-1,5-dibenzyloxycarbonyl-1,5,10-triazadecane 12.4 g (30.0 mmoles) of 1,5-dibenzyloxycarbonyl-1,5,10-triazadecane was dissolved in 200 ml of tetrahydrofuran, and 4.90 ml (35.0 mmoles) of triethylamine was added to the solution and 10.6 g (35.0 mmols) of phthalyglycine N-hydroxysuccinimide ester was further added to the mixture under cooling with ice. Then the mixture was allowed to react overnight at room temperature.

The reaction mixture was concentrated under reduced pressure, and the residue was dissolved in 1200 ml of ethyl acetate. The ethyl acetate solution was washed with a 5% aqueous solution of sodium hydrogen-carbonate, 0.5N hydrochloric acid, and a saturated aqueous solution of sodium chloride in this order. The ethyl acetate layer was dried over anhydrous sodium sulfate, and then, the desiccant was removed by filtration. The filtrate was concentrated under reduced pressure, and ethyl acetate and ethyl ether were added to the residue to crystallize it. The crystals formed were collected by filtration, and dried to obtain 14.6 g of the desired product in a yield of 81.0%.

mp: 102°–104° C.

NMR (DMSO-d$_6$): $\delta$=1.0–2.2 (b, 6H), 2.7–3.6 (b, 8H), 4.20 (s, 2H), 5.01 (s, 2H), 5.03 (s, 2H), 6.8–8.4 (b, 2H), 7.30 (s, 10H), 7.84 (s, 4H).

TLC (chloroform:methanol:acetic acid=95:5:3 v/v) Rf=0.4.

The starting material, 1,5-dibenzyloxycarbonyl-1,5,10-triazadecane, was synthesized in the following manner.

55.0 g (350 mmols) of 1-(4-aminobutyl)-hexahydro pyrimidine and 92.0 g (420 mmols) of ethoxycarbonylphthalimide were dissolved in 580 ml of dimethyl sulfoxide. To the solution was added 42.0 g (700 mmols) of glacial acetic acid, and the mixture was reacted overnight at room temperature with stirring. The reaction mixture was concentrated under reduced pressure of a vacuum pump. The residue was dissolved in 200 ml of distilled water, and the solution was adjusted to pH 1.0 by addition of concentrated hydrochloric acid, followed by concentrating the solution under reduced pressure. The residue was recrystallized from ethanol to obtain 46.9 g of 10-phthalyl-1,5,10-triazadecane dihydrochloride as a pale yellow substance in a yield of 38.5%.

mp: 244°–246° C.

NMR ($D_2O$): $\delta = 1.5$–2.0 (b, 4H), 2.0–2.5 (m, 2H) 2.9–3.5 (b, 6H), 3.5–3.9 (b, 2H) 7.76 (s, 4H).

27.9 (80.0 mmols) of the resulting 10-phthalyl-1,5,10-triazadecane dihydrochloride was dissolved in 300 ml of chloroform. To the solution were added 43.9 g (160 mmols) of benzyl-S-4,6-dimethylpyrimidin-2-yl thiolcarbonate and 17.8 g (17.6 mmols) of triethylamine, and the mixture was reacted for 6 hours at room temperature with stirring. The reaction mixture was washed with 1N hydrochloric acid and an aqueous solution of sodium chloride in this order, and dried over anhydrous magnesium sulfate. The dried solution was concentrated under reduced pressure to give 43.1 g (quantitative) of 10-phthalyl-1,5-dibenzyloxycarbonyl-1,5,10-triazadecane as a pale yellow oily substance.

NMR ($CDCl_3$): $\delta = 1.3$–2.1 (b, 6H), 1.9–3.9 (m, 8H) 5.10 (s, 4H), 7.30 (s, 5H), 7.33 (s, 5H) 7.73 (m, 4H).

31.3 g (57.6 mmols) of the resulting 10-phthalyl-1,5-dibenzyloxycarbonyl-1,5,10-triazadecane was dissolved in 600 ml of ethanol. 18.2 g (291 mmols) of 80% hydrazine hydrate was added to the solution, and the mixture was heated overnight under reflux. Precipitated crystals were removed by filtration, and the filtrate was concentrated under reduced pressure. The residue was dissolved in 300 ml of ethyl acetate, and the product was extracted with dilute hydrochloric acid. The aqueous layer was washed with ethyl acetate, then sodium carbonate was added to adjust the aqueous solution to pH 10. An oily material separated out was extracted with 500 ml of ethyl acetate, and the ethyl acetate layer was washed with a saturated aqueous solution of sodium chloride. The ethyl acetate layer was dried over anhydrous sodium sulfate, and concentrated under reduced pressure to obtain 20.1 g of 1,5-dibenzyloxycarbonyl-1,5,10-triazadecane in a yield of 84.8%.

NMR ($CDCl_3$): $\delta = 1.0$–2.3 (b, 8H), 2.3–2.9 (b, 2H) 2.9–3.5 (m, 6H), 5.05 (s, 2H), 5.07 (s, 2H), 5.1–6.1 (b, 1H), 7.30 (s, 10H).

(2)
10-Glycyl-1,5-dibenzyloxycarbonyl-1,5,10-triazadecane 370 ml of ethanol and 6.00 g (120 mmols) of hydrazine hydrate were added to 14.4 g (24.0 mmols) of 10-(N,N-phthalylglycyl)-1,5-dibenzyloxycarbonyl-1,5,10-triazadecane, and the mixture was refluxed for 2 hours. After the reaction, the insolubles were removed by filtration, and the filtrate was concentrated under reduced pressure. The resulting oily material was dissolved in 300 ml of ethyl acetate, and the solution was washed with a 5% aqueous solution of sodium hydrogencarbonate and distilled water in this order. The ethyl acetate layer was dried over anhydrous sodium sulfate, and the desiccant was removed by filtration. The filtrate was concentrated under reduced pressure to obtain 12.5 g of the desired product as an oily substance in a quantitative yield.

NMR ($CDCl_3$): $\delta = 0.8$–2.1 (b, 6H), 2.8–3.5 (b, 10H) 5.0–6.1 (b, 2H), 5.06 (s, 2H), 5.10 (s, 2H), 7.33 (s, 10H).

TLC (chloroform:methanol:acetic acid = 95:5:3 v/v): Rf = 0.1.

(3)
10-[N-(7-guanidinoheptanoyl)-glycyl]-1,5-dibenzyloxycarbonyl-1,5,10-triazadecane hydrochloride 12.5 g (24 mmols equivalent) of 10-glycyl-1,5-dibenzyloxycarbonyl-1,5,10-triazadecane was dissolved in 120 ml of tetrahydrofuran. 4.00 ml (29.0 mmols) of triethylamine was added to the solution. To the mixture was added a solution of 11.3 g (30 mmols equivalent) of 7-guanidinoheptanoic acid N-hydroxysuccinimide ester hydrochloride in 50 ml of dimethylformamide under cooling with ice, and the mixture was allowed to react overnight at room temperature. The reaction mixture was concentrated under reduced pressure, and the resulting oily residue was dissolved in 700 ml of ethyl acetate. The solution was washed with 0.5N hydrochloric acid saturated with sodium chloride, and then washed with a saturated aqueous solution of sodium chloride. An oily material precipitated during these washings was dissolved by addition of a small amount of ethanol. Then, the ethyl acetate layer was dried over anhydrous sodium sulfate, and the desiccant was removed by filtration. The filtrate was concentrated under reduced pressure to obtain 20.8 g (yield: quantitative) of the desired product as an oily substance.

NMR ($CDCl_3$): $\delta = 0.8$–1.9 (b, 14H), 1.9–2.4 (b, 2H), 2.7–3.5 (b, 10H), 3.5–4.0 (b, 2H), 5.04 (s, 4H), 6.2–8.0 (b, 8H), 7.27 (s, 10H).

TLC (n-butanol:acetic acid:water = 4:1:1 v/v) Rf = 0.3.

The 7-guanidinoheptanoic acid N-hydroxysuccinimide ester hydrochloride used above was synthesized in the following way:

50.0 g (0.344 mols) of 7-aminoheptanoic acid and 63.5 g (0.514 mol) of O-methylisourea sulfate were dissolved in 250 ml of 50% aqueous methanol (v/v). To the solution was added dropwise a solution of 34.3 g (0.858 mol) of sodium hdyroxide in 400 ml of water. Then, the mixture was heated overnight under reflux. The reaction mixture was concentrated to about a half volume under reduced pressure followed by cooling the concentrate to precipitate white crystals. The crystals were collected by filtration, and dried to give 42.6 g (yield: 66.1%) of 7-guanidinoheptanoic acid.

NMR ($D_2O + DCl$): $\delta = 1.0$–2.0 (b, 9H), 2.2–2.6 (m, 2H), 3.0–3.3 (m, 2H).

TLC (chloroform:methanol:17% ammonia water = 2:2:1) Rf = 0.5.

9-guanidinononanoic acid was synthesized likewise from 9-aminononanoic acid.

NMR (DMSO-$d_6$ + DCl): $\delta = 0.9$–1.9 (b, 12H) 2.0–2.4 (m, 2H), 2.9–3.4 (m, 2H).

TLC (n-propanol:water:29% ammonia water = 10:3:0.15 v/v) Rf = 0.6.

1.87 g (10 mmols) of 7-guanidinoheptanoic acid obtained in the preceding step was dissolved in 1N hydrochloric acid, and the solution was concentrated to dryness under reduced pressure, thereby obtaining 2.24 g (10 mmols) of 7-guanidinoheptanoic acid hydrochloride. This product was dissolved in 10 ml of dry dimethylformamide, and 2.06 g (10 mmols) of dicyclohexylcarbodiimide and 1.00 g (12 mmols) of N-hydroxysyccinimide were added in this order to the solution with stirring under cooling with ice. The reaction mixture was stirred for 30 minutes at 0° C., following at room temperature overnight. Dicyclohexylurea precipitated was removed by filtration, and the filtrate was concentrated under reduced pressure. Petroleum ether was added to the resulting oily material, and the mixture was stirred, followed by decanting the supernatant. This washing was repeated several times, and the washed oily material was concentrated under reduced pressure. The remaining solvent was removed under reduced pressure of a vacuum pump to obtain 3.65 g (guanitative) of crude 7-guanidinoheptanoic acid N-hydroxysuccinimide ester hydrochloride.

NMR (DMSO-d$_6$): δ=1.1–2.0 (b, 8H), 2.67 (t, 2H, J=6.0 Hz), 2.84 (s, 4H), 3.1 (m, 2H), 7.3 (b, 1H), 8.0 (b, 4H).

REFERENTIAL EXAMPLE 2

(1)

10-(N-tert-butoxycarbonyl-O-benzyl-L-seryl)-1,5-dibenzyloxycarbonyl-1,5,10-triazadecane 4.76 g (11.5 mmols) of 1,5-dibenzyloxycarbonyl-1,5,10-triazadecane was dissolved in 50 ml of ethyl acetate, and 1.04 g (10.3 mmols) of triethylamine was added to the solution. 5.87 g (15 mmols) of N-tert-butoxycarbonyl-O-benzyl-L-serine N-hydroxysuccinimide ester was added to the mixture under cooling with ice. Then the reaction mixture was allowed to react overnight at room temperature. 50 ml of ethyl acetate was added to the reaction mixture, and the resulting ethyl acetate solution was washed with a 5% aqueous solution of sodium hydrogencarbonate, 0.1N hydrochloric acid, and a saturated aqueous solution of sodium chloride in this order. The ethyl acetate layer was dried over anhydrous sodium sulfate, and the desiccant was removed by filtration. Concentrating the filtrate under reduced pressure gave 8.34 g (quantitative) of the desired product.

NMR (CDCl$_3$): δ=0.8–2.2 (b, 6H), 1.46 (s, 9H), 2.7–3.5 (b, 8H), 3.66 (m, 2H), 3.9–4.4 (b, 1H), 4.50 (s, 2H), 5.11 (s, 4H), 5.1–5.4 (b, 2H), 6.1–6.8 (b, 1H), 7.33 (s, 15H).

TLC (chloroform:methanol=9:1 v/v) Rf=0.8.

(2)

10-(O-benzyl-L-seryl)-1,5-dibenzyloxycarbonyl-1,5,10-triazadecane 8.00 g (11.5 mmols) of 10-(N-tert-butoxycarbonyl-O-benzyl-L-seryl)-1,5-dibenzyloxycarbonyl-1,5,10-triazadecane was dissolved in 8.0 ml of trifluoroacetic acid, and the solution was stirred for 3 hours at room temperature. The reaction mixture was concentrated under reduced pressure, and the residual oil was dissolved in 200 ml of ethyl acetate. The solution was washed with a 5% aqueous solution of sodium hydrogencarbonate and distilled water in this order, and the ethyl acetate layer was dried over anhydrous sodium sulfate. After the desiccant was removed by filtration, the filtrate was concentrated under reduced pressure to obtain 6.82 g (quantitative) of the desired product as an oily substance.

NMR (CDCl$_3$): δ=1.2–2.0 (b, 6H), 1.74 (s, 2H), 2.8–3.5 (b, 8H), 3.64 (m, 3H), 4.51 (s, 2H), 5.12 (s, 4H), 4.6–6.0 (b, 2H), 7.33 (s, 15H).

TLC (chloroform:methanol=9:1 v/v) Rf=0.5.

(3)

10-[N-(7-guanidinoheptanoyl)-O-benzyl-L-seryl]-1,5-dibenzyloxycarbonyl-1,5,10-triazadecane hydrochloride 3.56 g (6.03 mmols) of 10-(O-benzyl-L-seryl)-1,5-dibenzyloxycarbonyl-1,5,10-triazadecane was dissolved in 30 ml of tetrahydrofuran. To the solution cooled with ice, 0.61 g (6.03 mmols) of triethylamine was added. To the mixture was further added a solution of 6.14 g (7 mmols equivalent) of 7-guanidinoheptanoic acid p-nitrophenyl ester trifluoroacetate dissolved in 10 ml of tetrahydrofuran. The mixture was reacted overnight at room temperature then it was concentrated under reduced pressure, and the residual oil was dissolved in 150 ml of ethyl acetate. The solution was washed with a 10% aqueous solution of sodium carbonate, 0.5N hydrochloric acid, and a saturated aqueous solution of sodium chloride in this order. While washing, oily matter was precipitated, and it was dissolved by addition of a small amount of ethanol. Then, the ethyl acetate layer was dried over anhydrous sodium sulfate, and the desiccant was removed by filtration. Concentrating the filtrate under reduced pressure gave 4.77 g (guantitative) of the desired product as an oily substance.

NMR (DMSO-d$_6$): δ=1.0–2.0 (b, 14H), 2.0–2.4 (b, 2H), 2.7–3.5 (b, 10H), 3.58 (d, 2H, J=5 Hz), 4.2–4.8 (b, 1H), 4.47 (s, 2H), 5.01 (s, 2H), 5.04 (s, 2H), 6.8–8.3 (b, 8H), 7.27 (s, 5H), 7.30 (s, 10H).

TLC (chloroform:methanol:acetic acid=9:1:0.3 v/v) Rf=0.2.

When the similar procedure to Referential Example 1 or 2 was performed using other N-protected amino acids of general formula (IV) such as N-tert-butoxycarbonyl-O-benzyl-D-serine, N-tert-butoxycarbonyl-L-alanine, N-tert-butoxycarbonyl-β-alanine, N-tert-butoxycarbonyl-γ-aminobutyric acid, N-tert-butoxycarbonyl-L-proline, N-tert-butoxycarbonyl-L-leucine, N-tert-butoxycarbonyl-L-aspartic acid-β-benzyl ester, N-tert-butoxycarbonyl-L-glutamin, N-tert-butoxycarbonyl-N$^G$-nitro-L-arginine, N-tert-butoxycarbonyl-1-phenylalanine, N-butoxycarbonyl-N$^{im}$-benzyloxycarbonyl-L-histidine, and N-tert-butoxycarbonyl-O-benzyl-L-threonine, the corresponding 10-[N-(7-guanidinoheptanoyl)-R'$_2$]-1,5-dibenzyloxycarbonyl-1,5-dibenzyloxycarbonyl-1,5,10-triazadecane hydrochloride of the general formula (II) was obtained, respectively.

REFERENTIAL EXAMPLE 3

7-guanidino-3(S)-acetoxyheptanoic acid 3.55 g (14.8 mmols) of 7-guanidino-3(S)-hydroxyheptanoic acid was dissolved in 100 ml of glacial acetic acid, and hydrogen chloride gas was introduced to saturation at a temperature lower than room temperature. The reaction mixture was stirred for 2 hours at room temperature, and concentrated under reduced pressure. The above procedure was carried out two more times, and the residue was sufficiently dried to obtain the desired product in a quantitative yield.

NMR (DMSO-d$_6$): δ=1.0–1.9 (b, 6H), 2.00 (s, 3H), 2.4–2.8 (b, 2H), 2.9–3.4 (b, 2H), 4.9–5.3 (b, 1H), 6.6–9.3 (b, 6H).

TLC (alumina plate; n-butanol:pyridine:water:acetic acid=6:4:3:1 v/v), Rf=0.5.

REFERENTIAL EXAMPLE 4

(1)
10-(N-benzyloxycarbonyl-DL-homoseryl)-1,5-di-tert-butoxycarbonyl-1,5,10-triazadecane 3.76 g (16.0 mmols) of N-benzyloxycarbonyl-DL-homoserine lactone was dissolved in 20 ml of tetrahydrofuran. To the resulting solution was added a solution of 2.07 g (6.00 mmols) of 1,5-di-tert-butoxycarbonyl-1,5,10-triazadecane in 5 ml of tetrahydrofuran. The mixture was allowed to react for 3 days at room temperature. The reaction mixture was concentrated under reduced pressure. The residual oil was subjected to a column chlromatography of silica gel (Wako-Gel ®C-200, 400 g) using a mixed solvent of chloroform and methanol [chloroform:methanol=20:1 (v/v)] as a developer. Active fractions were collected and concentrated under reduced pressure to obtain 1.38 g (yield: 37.8%) of the desired product.

NMR (CDCl$_3$): δ=1.0–2.3 (b, 8H), 1.47 (s, 18H), 2.8–3.5 (b, 8H), 3.5–4.0 (b, 3H), 4.1–4.6 (m, 1H), 4.7–5.4 (b, 1H), 5.09 (s, 2H), 5.8–6.3 (b, 1H), 6.6–7.1 (b, 1H), 7.31 (s, 5H).

TLC (chloroform:methanol=20:1 v/v), Rf=0.2.

(2)
10-(DL-homoseryl)-1,5-di-tert-butoxycarbonyl-1,5,10-triazadecane 1.35 g (2.22 mmols) of 10-(N-benzyloxycarbonyl-DL-homoseryl)-1,5-di-tert-butoxycarbonyl-1,5,10-triazadecane was dissolved in 20 ml of methanol and was catalytically reduced over 0.1 g of palladium black for 8 hours at room temperature at atmospheric pressure. After the reaction, the catalyst was removed by filtration, and the filtrate was concentrated under reduced pressure. 0.91 g (86.4%) of the desired product was obtained as the residual oil.

NMR (CDCl$_3$) δ=1.1–2.2 (b, 10H), 1.47 (s, 18H), 2.8–3.5 (b, 9H), 3.5–4.0 (m, 3H), 4.6–5.6 (b, 1H), 7.4–7.9 (b, 1H).

TLC (chloroform:methanol=9:1 v/v), Rf=0.1.

(3)
10-[N-(7-guanidinoheptanoyl)-DL-homoseryl]-1,5-di-tert-butoxycarbonyl-1,5,10-triazadecane acetate 0.88 g (1.85 mmols) of 10-(DL-homoseryl)-1,5-di-tert-butoxy-carbonyl-1,5,10-triazadecane was dissolved in 5 ml of tetrahydrofuran, and 0.30 g (2.96 mmols) of triethylamine was added to the solution. A solution of 1.19 g (3.71 mmols) of 7-guanidinoheptanoic acid N-hydroxysuccinimide ester hydrochloride dissolved in 8 ml of dimethylformamide was added to the mixture under cooling with ice. Then the mixture was allowed to react overnight at room temperature. Then the reaction mixture was concentrated under reduced pressure. The residual oil was dissolved in 50 ml of a 2% aqueous solution of phosphoric acid, and the solution was washed with ethyl acetate. Sodium carbonate was added to the aqueous layer to adjust the pH to 10.5. Then, the aqueous layer was extracted with two 50 ml portions of ethyl acetate, and acetic acid was added to the ethyl acetate layer until it became substantially neutral. Concentrating the mixture under reduced pressure gave 1.08 g (86.4%) of the desired product as an oily substance.

NMR (DMSO-d$_6$): δ=0.9–2.0 (b, 16H), 1.43 (s, 18H), 1.84 (s, 3H), 2.0–2.4 (b, 2H), 2.7–3.7 (b, 11H), 3.37 (t, 2H), 4.1–4.6 (b, 1H), 6.3–8.4 (b, 8H).

TLC (chloroform:methanol:acetic acid=8:2:0.5 v/v) Rf=0.3.

REFERENTIAL EXAMPLE 5

10-[N-(7-guanidino-3(S)-acetoxyheptanoyl)-glycyl]-1,5-dibenzyloxycarbonyl-1,5,10-triazadecane hydrochloride Triethylamine (0.50 g) was added to a solution of 1.28 g (3.1 mmols) of 1,5-dibenzyloxycarbonyl-1,5,10-triazadecane and N-(7-guanidino-3(S)-acetoxyheptanoyl)-glycine N-hydroxysuccinimide ester hydrochloride in a mixed solvent of tetrahydrofuran (120 ml) and dimethylformamide (50 ml). The mixture was allowed to react overnight at room temperature. The reaction mixture was concentrated under reduced pressure. The residual oil was dissolved in 100 ml of ethyl acetate. The solution was washed with 0.5N hydrochloric acid and a saturated aqueous solution of sodium chloride in this order, if necessary, with adding ethanol little by little to avoid precipitation of an oily matter. The ethyl acetate layer was dried over anhydrous magnesium sulfate, and the desiccant was removed by filtration. The filtrate was concentrated under reduced pressure to obtain 1.91 g (83.9%) of the desired product as an oily substance.

REFERENTIAL EXAMPLE 6

10-[N-(9-guanidinononanoyl)-O-benzyl-L-seryl]-1,5-dibenzyloxycarbonyl-1,5,10-triazadecane hydrochloride 4.71 g (7.98 mmols) of 10-(O-benzyl-L-seryl)-1,5-dibenzyloxycarbonyl-1,5,10-triazadecane was dissolved in 30 ml of dimethylformamide, and 1.30 g (12.8 mmols) of triethylamine was added to the solution under cooling with ice. A dimethylformamide solution of 9-guanidinononanoic acid N-hydroxysuccinimide ester hydrochloride (12 mmols) was further added to the above solutoin. The resulting mixture was allowed to react overnight, then it was concentrated under reduced pressure, and the resulting oily residue was dissolved in 500 ml of ethyl acetate. The solution was washed with a 5% aqueous solution of sodium hydrogencarbonate, a saturated aqueous solution of sodium chloride, 0.2N hydrochloric acid, and a saturated aqueous solution of sodium chloride in this order, if necessary, with adding ethanol little by little to avoid the precipitation of oily matter. The ethyl acetate layer was dried over anhydrous sodium sulfate, and the desiccant was removed by filtration. The ethyl acetate layer was concentrated under reduced pressure to obtain 6.02 g (95.7%) of the desired product as an oily substance.

What is claimed is:

1. A compound represented by the general formula (I) or a salt thereof:

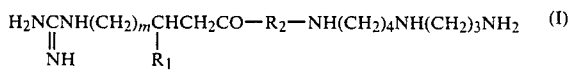

wherein R$_1$ represents a hydrogen atom, hydroxyl group, or an aliphatic acyloxy group having 1 to 10 carbon atoms, R$_2$ represents an amino acid residue (except for the residue of α-hydroxyglycine) formed by removing one hydrogen atom and hydroxyl group from respectively the α- or ω-amino group and the carboxyl group of an α- or ω-amino acid, said amino acid residue forming acid amide linkages with the adjacent carbonyl group and amino group, and m is an integer of 4 to 6.

2. A compound or a salt thereof according to claim 1, wherein $R_1$ is a hydrogen atom, hydroxyl group, or a (lower)acyloxy group and $R_2$ is a group represented by the general formula

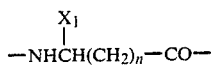
(a)

(wherein $X_1$ represents a hydrogen atom or an alkyl group having 1 to 6 carbon atoms, which alkyl group may have as substituent a hydroxyl, lower alkoxy, carboxyl, (lower)alkyloxycarbonyl, amino, guanidino, phenyl, hydroxy-substituted phenyl, 4-imidazolyl, 3-indolyl, mercapto, or (lower)alkylmercapto group, and n is an integer of 0 to 5) or by the general formula

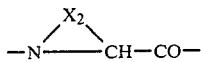
(b)

wherein $X_2$ represents a propylene group which may have a hydroxyl group as substituent.

3. A compound or a salt thereby according to claim 2, wherein $R_1$ is a hydrogen atom or hydroxyl group, $X_1$ is a hydrogen atom, hydroxymethyl group, guanidinopropyl group, or benzyl group, and n is 0.1 or 2.

4. 10-[N-(7-guanidinoheptanoyl)-glycyl]-1,5,10-triazadecane.

5. 10-[N-(7-guanidinoheptanoyl)-seryl]-1,5,10-triazadecane.

6. 10-[N-(7-guanidino-3-hydroxyheptanoyl)-seryl]-1,5,10-triazadecane.

* * * * *